US005545516A

United States Patent [19]
Wagner

[11] Patent Number: 5,545,516
[45] Date of Patent: Aug. 13, 1996

[54] INACTIVATION OF EXTRACELLULAR ENVELOPED VIRUSES IN BLOOD AND BLOOD COMPONENTS BY PHENTHIAZIN-5-IUM DYES PLUS LIGHT

[75] Inventor: Stephen J. Wagner, Columbia, Md.

[73] Assignee: The American National Red Cross, Washington, D.C.

[21] Appl. No.: 199,344

[22] Filed: Feb. 18, 1994

Related U.S. Application Data

[63] Continuation-in-part of Ser. No. 964,116, Oct. 21, 1992, abandoned, which is a continuation-in-part of Ser. No. 517,664, May 1, 1990, abandoned.

[51] Int. Cl.$^6$ .............................. A01N 1/02; A61K 35/14; A61K 35/16; A61K 35/18
[52] U.S. Cl. .............................. 435/2; 424/529; 424/530; 424/531; 424/532; 424/533
[58] Field of Search .............................. 435/2; 424/533, 424/529–532

[56] References Cited

U.S. PATENT DOCUMENTS

| | | | |
|---|---|---|---|
| 4,181,128 | 1/1980 | Swartz | 128/207.21 |
| 4,305,390 | 12/1981 | Swartz | 128/207.21 |
| 4,402,318 | 9/1983 | Swartz | 604/20 |
| 4,407,282 | 10/1983 | Swartz | 604/20 |
| 4,585,735 | 4/1986 | Meryman et al. | 435/2 |
| 4,727,027 | 2/1988 | Wiesehahn et al. | 435/173 |
| 4,748,120 | 5/1988 | Wiesehahn | 435/173 |
| 4,775,625 | 10/1988 | Sieber | 435/238 |
| 4,878,891 | 11/1989 | Judy et al. | 604/5 |
| 4,915,683 | 4/1990 | Sieber | 604/4 |
| 4,923,620 | 5/1990 | Pall | 210/767 |
| 4,950,665 | 8/1990 | Floyd | 514/222.8 |
| 5,006,642 | 4/1991 | Newman et al. | 530/383 |
| 5,120,649 | 6/1992 | Horowitz et al. | 435/173 |

FOREIGN PATENT DOCUMENTS

| | | |
|---|---|---|
| 275228 | 12/1986 | Japan. |
| 9013296 | 11/1990 | WIPO. |

OTHER PUBLICATIONS

Wagner et al., Red Cell Alterations Associated with Virucidal Methylene Blue Phototreatment, *Transfusion* 33: 30–36 (1993).

Lambrecht et al., Photoinactivation of Viruses in Human Fresh Plasma by Phenothiazine Dyes in Combination with Visible Light, *Vox–Sang* 60 : 207–213 (1991).

Friedman et al., Viral Inactivation and Reduction in Cellular Blood Products, *Ref. Fr. Transfus. Hemobiol.* 36 : 83–91 (1993).

Wagner et al., Approaches to the Reduction of Viral Infectivity in Cellular Blood Components and Single Donor Plasma, *Transfusion Medicine Reviews* V(1): 18–32 (1991).

Matthews et al., Photodynamic Therapy of Viral Contaminants with Potential for Blood Banking Applications, *Transfusion* 28(1) : 81–83 (1988).

Spikes et al., The Molecular Biology of Photodynamic Action: Sensitized Photoautoxidations in Biological Systems, *Adv. Radiat. Biol.* 3: 29–104, especially pp. 91–104 (1969).

Spikes, J. D., Photodynamic Reactions in Photomedicine, *The Science of Photomedicine* (Regan et al., eds.) Plenum Pub. Corp., N.Y., NY (1982).

Vodrážka et al., Photooxidation of Blood Protiens. VIII.* Photooxidation of Human Hemoglobin in the Presence of Sensitizers, *Coll. Czech. Chem. Commun.* 28: 2813–2816 (1961).

Menezes et al., Photodynamic Action of Methylene Blue: Repair and Mutation in *Eschericha coli, J. of Photochem. and Photobiol.* 5 : 505–517 (1990).

Girotti et al., Methylene Blue–Sensitized Photooxidation of Hemoglobin: Evidence for Cross–Link Formation, *Photochem. and Photobiol.* 29 : 1119–1125 (1979).

Girotti, A. W., Photosensitized Cross–Linking of Erythrocyte Membrane Protiens; Evidence Against Participation of Amino Groups in the Reaction, *Biochimica et Biophysica Acta* 602 : 45–56 (1980).

Sass et al., Accumulation of Methylene Blue by Metabolizing Erythrocytes, *J. Lab. & Clin. Med.* 69(3) : 447–455 (1967).

Zook et al., Covalent Cross–Linking of Ribosomal RNA and Proteins by Methylene Blue–Sensitized Photooxidation, *Biochimica et Biophysica Acta.* 517 : 400–406 (1978).

Yamamoto, N., Photodynamic Inactivation of Bacteriophage and Its Inhibiton, *J. Bacteriol.* 75 : 443–448 (1958).

Shortt et al. Photodynamic Action of Methylene Blue on Fixed Rabies Virus, *Ind. Jour. Med. Res., XXI*, 3 : 581–585 (1934).

Chang et al., Eczema Herpeticum: Treatment with Methylene Blue and Light, *Arch. Dermatol.* 111 : 1174–1175 (1975).

Hiatt et al., Inactivation of Viruses by the Photodynamic Action of Toluidine Blue, *J. Immunol.* 84 : 480–484 (1960).

Wallis et al., Irreversible Photosensitization of Viruses, *Virology* 23: 520–527 (1964).

Wallis et al., Influenza Vaccine Prepared by Photodynamic Inactivation of Virus, *J. Immunol.* 91 : 677–682 (1963).

(List continued on next page.)

*Primary Examiner*—Marian C. Knode
*Assistant Examiner*—S. Saucier
*Attorney, Agent, or Firm*—Sterne, Kessler, Goldstein & Fox

[57] ABSTRACT

This invention provides methods for inactivating pathogenic contaminants in whole blood, plasma, cellular blood components, or in any combination thereof, by adding a phenthiazin-5-ium dye(s) thereto and irradiating said dye-containing composition for an effective length of time with light of wavelengths from 560 to 800 nm or red light, of an effective intensity, whereby the irradiation in conjunction with the dye(s) inactivate substantially all pathogenic contaminants contained therein. The methods of this invention inactivate pathogenic contaminants, such as viruses, bacteria and parasites, without substantially altering the whole blood, plasma, cellular blood components, or combinations thereof, such that they are suitable for transfusion.

33 Claims, 5 Drawing Sheets

OTHER PUBLICATIONS

Gerba et al., Application of Photodynamic Oxidation to the Disinfection of Tapwater, Seawater, and Sewage Contaminated with Poliovirus, *Photochem. and Photobiol.* 26 : 499–504 (1977).

Sinkovics et al., Some Properties of the Photodynamically Inactivated Rauscher Mouse Leukemia Virus, *Cancer Research* 25 : 624–627 (1965).

Wallis et al., Photodynamic Inactivation of Poliovirus, *Virology* 21 : 332–341 (1963).

Thormar et al., Photoinactivation of Visna Virus, *Acta Path. et Microbiol. Scandinav.* 62 : 461–462 (1964).

Alter et al., Photochemical Decontamination of Blood Components Containing Hepatitis B and Non-A, Non-B Virus, *The Lancet* Dec. 24/31 : 1446–1450 (1988).

Wallis et al., Photodynamic Inactivation of Animal Viruses: A Review, *Photochem. and Photobiol.* 4 : 159–170 (1965).

Hiatt, C. W., Photodynamic Inactivation of Viruses, *Trans. N.Y. Acad. Sci.* 23 : 66–78 (1960).

Badylak et al., Photodynamic Inactivation of Pseudorabies Virus with Methylene Blue Dye, Light, and Electricity, *J. Clin. Microbiol.* 17(2) : 374–376 (1983).

Swartz et al., Inactivation of Herpes Simplex Virus with Methylene Blue, Light and Electricity, *Pro. Soc. Exper. Biol. and Med.* 161 : 204–209 (1979).

Sadoff et al., Experimental 6 $\log_{10}$ White Cell–Reduction Filters for Red Cells, *Transfusion* 32(2) : 129–133 (1992).

Rawal et al., Evaluation of Leukocyte Removal Filters Modelled by Use of HIV–Infected Cells and DNA Amplification, *Blood* 76(10) : 2159–2161 (1990).

Meryman et al., *Vox Sang.* 18 : 88–98 (1991).

Floyd et al., *Arch. Biochem Biophys.* 273 : 106–111 (1989).

Prodouz, *Transfusion* 29 : 42S (1989).

Parrish, Photobiology and Immunology in *The Effect of Ultraviolet Radiation on the Immune System*, Johnson and Johnson Baby Products Company, USA; pp. 3–20 (1983).

Prince et al., *Rev. Infect. Dis.* 5 : 92–107 (1983).

Girotti, *Biochim. Biophys. Acta* 602 : 45–56 (1980).

Ganong, Circulating Body Fluids in *Review of Medical Physiology*, Lange Medical Publications, Los Altos, Calif., pp. 396–414, 410 (1979).

Snipes et al., *Photochem. Photobiol.* 29 : 785–790 (1979).

Yen et al., *J. Gen. Virol.* 41 : 273–281 (1978).

De Goeij et al., *Clin. Chim. Acta* 71 : 485–494 (1976).

Chang et al., *Proc. Soc. Exp. Biol. Med.* 148 : 291–293 (1975).

Haschemeyer et al., Optical Methods in *Protiens*, John Wiley & Sons, Inc., New York, pp. 217–253 (1973).

Hiatt, Methods for Photoinactivation of Viruses in *Concepts in Radiation Cell Biology* pp. 57–89 (1972).

Sass et al., *J. Lab. Clin. Med.* 73 : 744–752 (1969).

Simon et al., *Arch. Biochem. Biophys.* 105 : 197–206 (1964).

Perdrau et al., *Proc. Roy. Soc. London (Biol.)* 122 : 288–298 (1933).

Clifton, *Proc. Soc. Exper. Biol. Med.* 28 : 745–746 (1931).

Heinmets et al., Research Report (WRAIR–53–55), Inactivation of Viruses in Plasma by Photosensitized Oxidation, Walter Reed Army Medical Center, Washington, DC, pp. 1–16 (1955).

MacRobert et al., *Ciba Foundation Symposium* 146, Photosensitizing Compounds: Their Chemistry, Biology and Clinical Use, John Wiley & Sons, New York, NY, pp. 4–16 (1989).

Menezes et al., *J. Photochemistry and Photobiology, B: Biology*, 5 : 505–517 (1990).

INACTIVATION OF EXTRACELLULAR ENVELOPED VIRUSES IN BLOOD AND BLOOD COMPONENTS BY PHENTHIAZIN-5-IUM DYES PLUS LIGHT

This application is a CIP of Ser. No. 07/964,116, filed Oct. 21, 1992, now abandoned which is a CIP of Ser. No. 07/517,664, filed May 1, 1990, now abandoned.

FIELD OF INVENTION

This invention is directed to methods for inactivating viruses and other pathogenic contaminants in transfusible blood and blood components.

BACKGROUND OF INVENTION

Among the risks inherent in handling or being transfused with blood, blood proteins, or other blood components is the risk of infection from pathogenic contaminants, including human immunodeficiency viruses (HIV) and hepatitis viruses. Virucidal methods, including heat, solvent-detergent, and gamma irradiation have been used to produce non-infectious plasma derivatives, but such methods are ineffective or are too harsh to be used for decontamination of whole blood, red cells or platelets. Any treatment that damages or introduces harmful or undesirable contaminants into the product is unsuitable to decontaminate a product intended for transfusion.

Because of the critical need for transfusible red blood cells, it is of great importance to develop methods that can be readily used to decontaminate cellular blood components and whole blood without substantially or irreversibly altering or harming them.

At least 75% of the red cells that are transfused must be circulating 24 hours after their transfusion. The shelf-life and suitability of red blood cells for transfusion is determined on this basis. The concentrations of ATP and of 2,3 diphosphoglycerate (2,3 DPG) and the morphology of red cells serve as indicators of the suitability of such cells for transfusion. During prolonged storage or as a result of harsh treatments, human red blood cells undergo changes that include decreases in the cellular levels of ATP and 2,3 DPG and changes in cellular morphology. For example, during storage, the concentration of ATP, after a brief initial rise, progressively declines to about 50% of its initial level. The fluidity of the cell membranes of red cells, which is essential for the passage of such cells through the narrow channels in the spleen and liver, is correlated with the level of ATP. As the level of ATP declines, the fluidity of the cellular membrane decreases rendering the cells unsuitable for transfusion. The level of 2,3 DPG falls rapidly after about 3 or 4 days of storage and approaches zero after about 10 days. 2,3 DPG is associated with the ability of the hemoglobin in the red cells to deliver oxygen to the tissues.

Solutions that prolong the shelf life of red cells are known (Meryman et al., U.S. Pat. No. 4,585,735 (incorporated herein by reference)). Typically such solutions contain citrate, phosphate, glucose, adenine, and other ingredients and function to prolong shelf life by maintaining the levels of ATP and 2,3 DPG in the cells. Solutions that contain a penetrating salt, such as ammonium acetate, in addition to phosphate, glucose, and adenine, and that are hypotonic with respect to molecules that are unable to penetrate the cell membrane, have been shown to maintain the levels of ATP for more than 100 days of refrigeration (Meryman et al., supra).

Decontamination treatments that inactivate contaminating pathogens, but that do not harm the cellular fractions of blood are not readily available. Decontamination procedures presently include the use of photosensitizers, which, in the presence of oxygen and upon exposure to light, including wavelengths absorbed by the photosensitizer, inactivate viruses (EP 0 196 515, published 08.10.86, to Baxter Travenol Laboratories, Inc.). Typically such photochemicals are dyes or other compounds that readily absorb UV or visible light in the presence of oxygen. Such compounds include psoralen derivatives (U.S. Pat. No. 4,748,120 to Wiesehahn), porphyrin derivatives (U.S. Pat. No. 4,878,891 to Judy et al.) and other photosensitizers. Often, however, such treatment also damages cellular blood components.

The virucidal activity of these compounds is realized when the absorption spectrum of the photosensitizer does not significantly overlap the absorption spectra of pigments present in the blood. In order to minimize cellular damage, it is advantageous if the photosensitizer selectively binds to a component of the virus that is not present in red cells or platelets or, if present therein, that is not essential to red cells' or platelets' function, and is not toxic to these cells. It is also preferable if the photodynamic treatment inactivates extracellular and intracellular virus as well as cells containing provirus. It is beneficial if the virucidal activity of the photosensitizer is not inhibited by the presence of plasma proteins.

Photochemicals such as the psoralens (U.S. Pat. No. 4,748,120 to Wiesehahn) damage nucleic acids in the presence of light while the porphyrins (U.S. Pat. No. 4,878,891 to Judy et al.) and merocyanine 540 (MC 540), (U.S. Pat. No. 4,775,625 to Sieber) cause membrane damage in the presence of light and oxygen and thereby inactivate viruses and bacteriophages.

Among the problems that occur during decontamination with psoralen and porphyrin derivatives is that they apparently bind to blood components, such as albumin (Prodouz, *Transfusion* 29:42S (1989)). Prodouz studied the effect of MC 540 on platelets and the influence of albumin on MC 540's virucidal activity. Platelets exhibited a MC dose-dependent decrease in response to thrombin in the absence of light. In the presence of light and MC 540, the platelets aggregated. Albumin prevented that aggregation and inhibited the inactivation of viral contaminants by MC 540 plus light.

Similarly, because of such competitive inhibition reactions with blood or plasma components, other dyes have not been suitable for decontaminating blood, cellular blood components, or any blood derived products containing high plasma concentrations. As the plasma concentration increases, the percentage of viral inactivation substantially decreases.

The phenothiazin-5-ium dyes, which include methylene blue, toluidine blue O, thionine, azure A, azure B, and azure C, are useful for inactivating animal viruses (Swartz, U.S. Pat. Nos. 4,407,282, 4,402,318, 4,305,390, and 4,181,128). These dyes, however, have not been used to inactivate pathogens in whole blood or in cellular blood components because red cells readily take up or bind such dyes (Sass et al., *J. Lab. Clin. Med.* 73:744–752 (1969)). Methylene blue and visible light damage guanine residues of nucleic acids (Simon et al., *J. Mol. Biol.* 4:488–499 (1962)). Methylene blue and white light produce 8-hydroxyguanine in DNA (Floyd et at., *Arch. Biochim. Biophys.* 273:106–111 (1989)). In addition, Girotti demonstrated that photosensitized oxidation of biological membranes is deleterious to membrane structure and function and showed that methylene blue cross-links the membrane protein, spectrin, in erythrocytes exposed to visible light and oxygen (Girotti, *Biochim. Biophys. Acta.* 602:45–56 (1980)). Thus, because of these and other potentially deleterious effects, phenothiazin-5-ium dyes have not been selected as photosensitizers for decontaminating blood or cellular blood components.

No method has proven fully successful for decontaminating whole blood, cellular blood components during storage, or compositions containing concentrated blood components, including high levels of plasma. Because of the AIDS epidemic there is, however, an acute need to develop a safe method whereby pathogenic contaminants, particularly HIV and hepatitis, in blood or in cellular blood components can be inactivated without rendering the blood or cellular blood components unsuitable for transfusion.

SUMMARY OF THE INVENTION

It is one object of this invention to provide a method for decontaminating whole blood or cellular blood components, comprising: adding an adequate amount of at least one phenothiazin-5-ium dye to said whole blood or cellular blood components to produce therein an effective decontaminating concentration of said dye(s), which concentration is acceptable for transfusion; and irradiating said phenothiazin-5-ium dye-containing whole blood or cellular blood components for an effective length of time, with light of an effective intensity and of wavelengths from 560 to 800 nm, whereby said irradiation in conjunction with said dye(s) inactivate substantially all pathogenic contaminants in said whole blood or cellular blood components, without substantially or irreversibly harming said whole blood or cellular blood components.

It is another object of this invention to provide a method for decontaminating whole blood or cellular blood components, when said whole blood or cellular blood components are in a transfusible composition.

It is another object of this invention to provide a method for decontaminating plasma-containing compositions, comprising: adding an adequate amount of at least one phenothiazin-5-ium dye to said plasma-containing compositions to produce therein an effective decontaminating concentration of said dye(s), which concentration is acceptable for transfusion; and irradiating said phenothiazin-5-ium dye- and plasma-containing compositions for an effective length of time, with light of an effective intensity and of wavelengths from 560 to 800 nm, whereby said irradiation in conjunction with said dye(s) inactivate substantially all pathogenic contaminants in said plasma-containing compositions, without substantially or irreversibly harming said plasma-containing compositions.

It is another object of this invention to provide a method for decontaminating transfusible compositions, comprising: adding an adequate amount of at least one phenothiazin-5-ium dye to said transfusible compositions to produce therein an effective decontaminating concentration of said dye(s), which concentration is acceptable for transfusion; and irradiating said phenothiazin-5-ium dye-containing transfusible compositions for an effective length of time, with light of an effective intensity and of wavelengths from 560 to 800 nm, whereby said irradiation in conjunction with said dye(s) inactivate substantially all pathogenic contaminants in said transfusible compositions, without substantially or irreversibly harming said transfusible compositions.

It is another object of this invention to provide a method for decontaminating leukocyte-containing transfusible compositions, comprising: leukodepleting said transfusible compositions; adding an adequate amount of at least one phenothiazin-5-ium dye to said leukodepleted compositions to produce therein an effective decontaminating concentration of said dye(s), which concentration is acceptable for transfusion; and irradiating said phenothiazin-5-ium dye-containing, leukodepleted transfusible compositions for an effective length of time with light of effective intensity and wavelengths of from 560 to 800 nm, whereby said irradiation in conjunction with said dye(s) inactivate substantially all pathogenic contaminants in said leukodepleted, transfusible compositions, without substantially or irreversibly harming said transfusible compositions.

This invention significantly improves the procedure for decontaminating whole blood, cellular blood components and plasma by providing methods that produce non-infectious whole blood, cellular blood components, or plasma which can be transfused without the need for diluting or removing the photosensitizing dye.

In practicing this invention at least one phenothiazin-5-ium dye such as methylene blue, toluidine blue O, thionine, azure A, azure B, azure C, or any other phenothiazin-5-ium dye known to those of skill in the art, is added to the whole blood, cellular blood component, plasma, or composition that contains whole blood, cellular blood component, or plasma. The mixture is then iradiated with effective wavelengths of light, such as from 560 to 800 nm or red light, and any pathogenic contaminant, such as a virus, bacteria or parasite, is inactivated.

DESCRIPTION OF THE PREFERRED EMBODIMENTS

Figure 1:
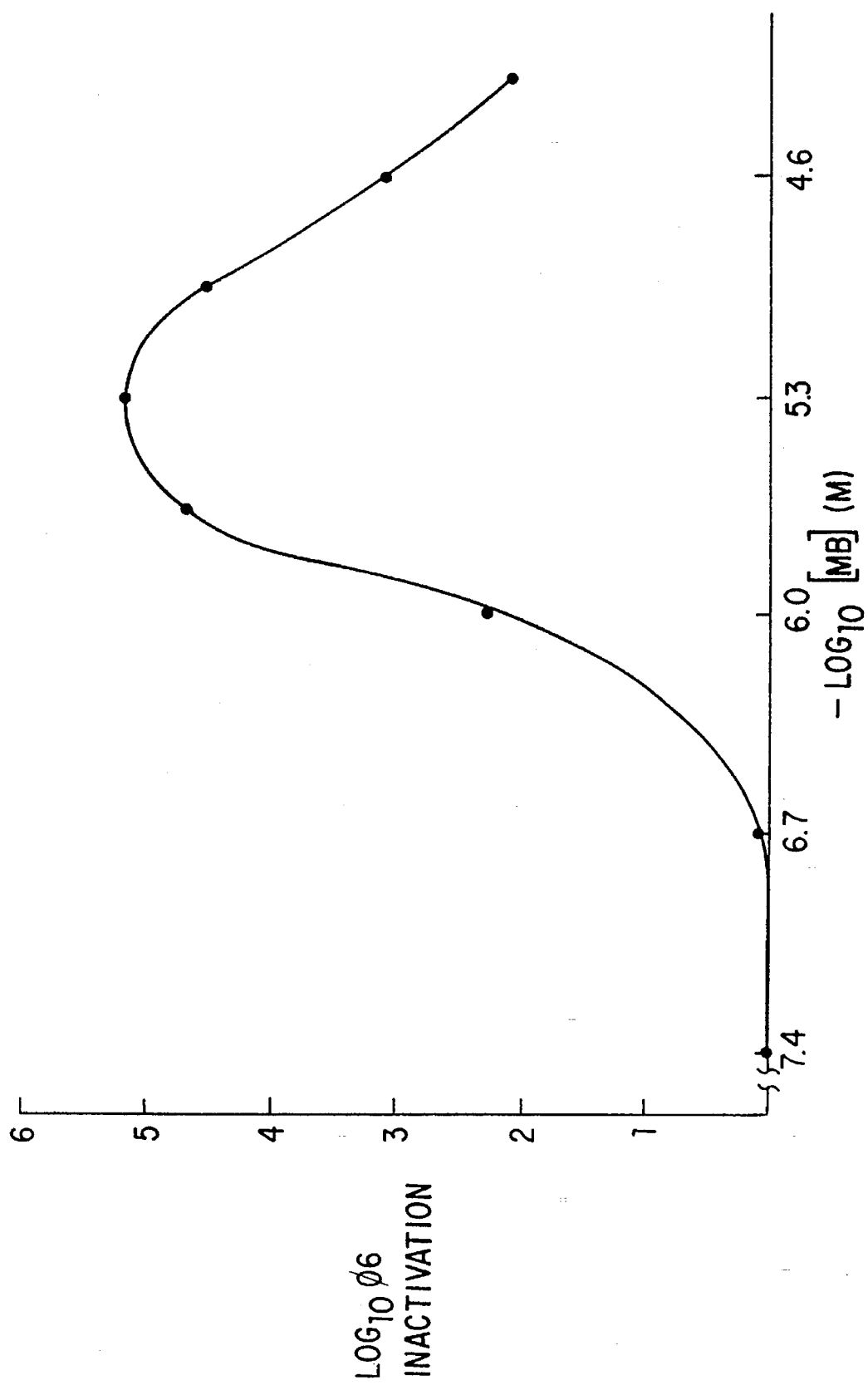
FIG. 1 presents the dependence of inactivation of bacteriophage Φ6 in 16% solution of plasma in Unisol as a function of methylene blue concentration in the sample. Samples containing the bacteriophage, plasma, and increasing concentrations of methylene blue were exposed for 4 minutes at a fluence rate of 2 mW/cm$^2$ of sample delivered by General Electric F15T8-R bulbs.

Unless defined otherwise, all technical and scientific terms used herein have the same meaning as is commonly understood by one of ordinary skill in the an to which this invention belongs. All publications mentioned herein are incorporated by reference thereto.

As used herein, a pathogenic contaminant of blood or blood component is a contaminant that, upon handling or transfusion into a recipient may cause disease in the handler or recipient. Examples of such pathogens include, but are not limited to, retroviruses, such as HIV, and hepatitis viruses.

As used herein, a blood component is a component that is separated from blood and includes, but is not limited to red blood cells and platelets, blood clotting factors, plasma, enzymes, plasminogen, and immunoglobulins. A cellular blood component is a component of blood, such as a red blood cell, that is a cell. A blood protein is a protein that is normally found in blood. Examples of such proteins are blood factors VII and VIII. Such proteins and components are well-known to those of skill in the art.

As used herein, a composition containing a cellular blood component or a blood protein is a composition that contains a biologically compatible solution and a blood component, blood protein, or mixtures thereof. Such compositions may also contain plasma and, if not leukodepleted, leukocytes. If such compositions are leukodepleted, the concentration of leukocytes is reduced by a specified amount.

As used herein a transfusible composition is a composition that can be transfused into the blood stream and that contains blood, at least one cellular blood component, concentrated plasma, or mixtures of blood, cellular blood components, and plasma.

As used herein, decontamination refers to a process whereby pathogens, such as viral contaminants, are rendered noninfectious, so that blood or a composition that contains blood, a blood component or blood protein can be transfused or manipulated without harming or infecting anyone exposed thereto.

As used herein, a pathogen includes any replicable agent that infects or occurs in blood or blood components. Such pathogens include any virus, bacterium, or parasite known to those of skill in the art to be found in blood or products derived from blood. Examples of pathogens include but are not limited to: bacteria, such as Streptococcus species, Escherichia species, and Bacillus species; viruses, such as human immunodeficiency viruses, other retroviruses, herpes viruses, paramyxoviruses, cytomegaloviruses, hepatitis viruses, including hepatitis A, hepatitis B, and hepatitis C, pox viruses, and toga viruses; and parasites, such as malarial parasites, including Plasmodium species, and trypanosomal parasites.

As used herein, the ratio of the titer of the control sample to the titer of virus in each of the treated samples, is herein called Φ6 inactivation. The $log_{10}$ of this ratio is herein called $log_{10}$ inactivation. Typically, a $log_{10}$ inactivation of at least about 5 to 6 logs indicates that the treated sample has been decontaminated.

As used herein, a composition in which substantially all of the contaminating pathogens have been inactivated is one in which the concentration of active pathogen has been decreased by a factor of at least about 5 to 6 logs. A composition in which substantially all of the contaminating pathogens have been inactivated is, thus, decontaminated.

As used herein, fluence is a measure of the energy per unit area of sample and is typically measured in $joules/cm^2$. Fluence rate is a measure of the wattage of light that strikes a unit area of the sample. For example, it can be measured as milliwats (mW)/per $cm^2$. Fluence rate can also be measured as the amount of energy that strikes the sample in a given amount of time and may be measured as $joules/cm^2$ per unit time of exposure.

As used herein, phenothiazin-5-ium dyes include any dye that one having skill in the art would consider a member of that class. This class includes, but is not limited to, methylene blue, toluidine blue O, thionine, azure A, azure B and azure C.

As used herein, plasma can be prepared by any method known to those of skill in the an. For example, it can be prepared by centrifuging blood at a force that pellets the cells and forms an interface between the red cells, the buffy coat, which contains leukocytes, and the plasma which is above.

As used herein, leukocyte depleted blood component is blood component that has been filtered through a filter that depletes the concentration of leukocytes in the plasma by a factor of $10^2$ to $10^5$. Such filters are identified by the log of the factor by which the plasma or other blood component is depleted of leukocytes.

As used herein, extracellular pH is the pH of the medium in which red blood cells or other cellular blood components are stored or maintained.

As used herein, a biologically compatible solution or a biologically compatible buffered solution is a buffered solution in which cells that are contacted therewith retain viability. Contacting includes any process in which the cells are in some manner exposed to the buffered solution and includes, but is not limited to, suspension of the cells in the buffered solution. A biologically compatible buffered solution has a pH and a salt concentration that is suitable for maintaining the integrity of the cell membrane and does not inhibit or destroy the biological and physiological reactions of the cells contacted therewith. Typically a biologically compatible buffered solution has a pH between 5 and 8.5 and is isotonic or only moderately hypotonic or hypertonic. Biologically compatible buffered solutions are readily available to those of skill in the art. Examples of biologically compatible buffered solutions include, but are not limited to those listed in Table I, infra.

As a first step when practicing any of the embodiments of the invention disclosed herein, blood is drawn from a donor into a suitable biologically compatible buffered solution that is known to those of skill in the art. The whole blood may then be subjected to a decontamination process in accordance with this invention. Alternatively, the blood may be separated into its components, including, but not limited to, plasma, platelets and red blood cells by any method known to those of skill in the art.

For example, blood can be centrifuged for a sufficient time and at a sufficient centrifugal force to form a pellet containing the red blood cells. Leukocytes collect primarily at the interface of the pellet and supernatant in the buffy coat region. The supernatant, which contains plasma, platelets, and other blood components, may then be removed and centrifuged at a higher centrifugal force, whereby the platelets pellet.

Human blood normally contains about $7 \times 10^9$ leukocytes per liter. The concentration of leukocytes, which pellet with the red cells, can be decreased by filtering through a filter that decreases their concentration by selected orders of magnitude. Leukocytes can also be removed from each of the components by filtration through an appropriate filter that removes them from the solution. When practicing the method of this invention, if leukocytes are not removed from the composition that is being treated, the concentration of dye, the light intensity, and/or the time of irradiation must be somewhat increased. It is well within the level of skill in the art to ascertain the amount by which any or all of such parameters should be adjusted. It has, however, been discovered that plasma proteins do not affect the inactivation reactions that occur when practicing the method of this invention. Thus, the values of these parameters need not be adjusted for the presence of plasma proteins.

In accordance with this invention, the composition of blood, cellular blood components, or concentrated plasma, a composition containing blood, cellular blood components or mixtures of cellular blood components, plasma and leukocytes or any other composition containing blood or blood components, may be obtained or prepared as described above or by any means or method known to those of skill in the art.

In one embodiment of this invention such compositions are obtained in, prepared or introduced into gas permeable blood preservation bags, which are sealed and flattened to a width sufficiently narrow to permit light to pass through and irradiate the contents, whereby any pathogen present in the bag would be irradiated. Any such blood bag known to those of skill in the art may be used as long as there is sufficient oxygen present in the bag to react with the photosensitizer and the bag is transparent to the selected wavelength of light.

The composition that is decontaminated may include any suitable biologically compatible buffer known to those of skill in the art. Examples of such buffers include, but are not limited to Unisol and ARC 8 (see, TABLE 1, infra.).

The dyes or photosensitizer compounds of this invention include the phenothiazin-5-ium dyes. Any such dye known to those of skill in the art may be used. Examples of such dyes include, but are not limited to, methylene blue, toluidine blue O, azure A, azure B, azure C and thionine. An effective amount of at least one selected dye is introduced into the composition. Ideally the selected dye is non-toxic and the effective concentration is acceptable for transfusion so that the treated blood or blood component does not require additional manipulation to remove the dye and thereby risk contamination.

The effective concentration of dye to be used can be determined by one of skill in the art. Generally it is in the range of, but is not limited to, 0.2 to 50 $\mu$M.

In a preferred embodiment methylene blue may be selected. Methylene blue is used therapeutically to treat methemoglobinemia at a dosage of 1 mg/kg of body weight to a maximum recommended dosage of 2 mg/kg. Thus, blood or cellular blood components or other compositions treated in accordance with this invention can be directly transfused, as long as the final dosage of methylene blue is less than about 2 mg/kg of body weight.

In a preferred embodiment of this invention methylene blue is introduced into the composition at a concentration of about 1 $\mu$M to about 25 $\mu$M. Thus, when used in accordance with this invention the amount of methylene blue needed for inactivation is substantially less, about twenty-five fold less, than the maximum recommended dosage. For example, transfusion of ten units of red cells at a 55% hematocrit that have been treated with 5 $\mu$M methylene blue in accordance with this invention would only provide a dose of methylene blue of 0.08 mg/kg, which is substantially less than the maximum recommended dosage.

The mixture of the blood or blood component composition and dye is then irradiated for a sufficient time with an appropriate wavelength or mixture of wavelengths, whereby pathogenic contaminants in the composition are inactivated. Such wavelength is one that is absorbed by the dye, but that does not damage the blood or blood components present in the composition. It is well within the level of skill in the art to select such wavelength and to ascertain a sufficient time for inactivation. For example, the selected wavelength is based on the absorption profile of the selected dye or dyes and is one that does not substantially damage the cellular components of the composition selected for decontamination. Further, model viral systems are known to those of skill in the art which may be used to test the selected dye and light source. Such model viral systems include, but are not limited to the enveloped bacteriophage, bacteriophage Φ6, vesicular stomatitis virus (VSV), which is an animal virus that contains it genome encoded in DNA, and Sindbis virus, which is an animal virus that contains its genome encoded as RNA. Based on the effective values of parameters, such as wavelength and light intensity, measured for such model systems, one having skill in the art can select the values for these parameters for use in practice. For example, one having skill in the art would know that if the intensity or power of the light source is decreased, a greater concentration of dye and/or longer exposure time should be used.

In one embodiment of this invention, red blood cells, which have been leukodepleted with a five log filter, are suspended in ARC 8 at a hematocrit of about 15 to 55%, introduced into gas permeable blood preservation bags in an amount such that the filled bag has a thickness of about 4 mm, and treated with methylene blue at a concentration of about 1 $\mu$M up to about 25 $\mu$M and red light of wavelength (560 to 800 nm) at a sufficient intensity and a long enough time, such as 3.6 joule/cm$^2$ for about 60 minutes, to inactivate pathogenic contaminants in the red blood cells and ARC 8 solution. The virucidal activity of the methylene blue and light treatment is not affected by the presence of up to 100% plasma but was reduced by the presence of leukocytes. Accordingly, in the presence of leukocytes, light intensity, dye concentration, and/or irradiation time must be increased in order to ensure that the sample is decontaminated.

In other embodiments of this invention, compositions containing platelets and compositions containing high concentrations of plasma may be decontaminated by exposure for a sufficient time to an effective concentration of a phenothiazin-5-ium dye plus an effective amount of an appropriate wavelength of light.

Following treatment in accordance with the method of this invention, the blood, cellular blood components or composition may be stored or transfused. Alternatively, after treatment of compositions such as red cell preparations or platelet-rich plasma, the composition can be centrifuged at a force sufficient to pellet the cellular components. The supernatant can be removed following centrifugation and the cells resuspended to reduce the concentration of residual photosensitizer and any reaction products.

The following examples are included for illustrative purposes only and are not intended to limit the scope of the invention.

TABLE 1

TYPICAL BIOLOGICALLY COMPATIBLE BUFFERED SOLUTIONS
SOLUTION CONCENTRATION

| Ingredient | CPDA-1* (mM) | UNISOL (mM) | ARC 8 (mM) |
|---|---|---|---|
| NaCitrate | 89.6 | 17.3 | 33.3 |
| cit. acid** | 15.6 | 2.7 | — |
| glucose | — | — | 139 |
| dextrose | 161.0 | 35.5 | — |
| $NaH_2PO_4$ | 16.1 | — | 2.9 |
| $NaHPO_4$ | — | 3.0 | 12.0 |
| Adenine | 2.0 | 2.2 | 2.0 |
| Mannitol | — | — | — |
| NaCl | — | 110.4 | — |
| KCl | — | 5.1 | — |
| $CaCl_2$ | — | 1.7 | — |
| $MgCl_2$ | — | 4.0 | — |
| $NaHCO_3$ | — | 40.0 | — |
| pH | 5.7 | 7.4 | 7.4 |

*CPDA-1 is sold by Baxter Travenol.
**cit. acid means citric acid.

EXAMPLE 1

Materials:

Plasma was prepared from human blood by centrifugation to pellet the red cells and to remove the platelets. Leukocytes were removed by filtration with a log filter as indicated.

Methylene Blue was reagent or USP grade.

Unisol and ARC 8 are prepared as indicated in TABLE 1.

Blood bags were gas permeable.

Bacteriophage Φ6 stock solution was prepared from lysates of the HB10Y strain of *Pseudomonas phaseolicola*. At the concentrations used, methylene blue was not harmful to virus in the absence of light (Tables 2, 4, 8, and 10).

Platelet-poor human plasma was diluted to a final concentration of 16% in Unisol. Forty μl of bacteriophage Φ6 stock solution was added to 4 ml of sample and varying amounts of 1 mg/ml methylene blue solution were added to each sample. The samples were incubated at room temperature and then exposed for 4 minutes to light delivered by General Electric F15T8-R bulbs at a fluence rate of 2 $mW/cm^2$ of sample.

After the light treatment, the samples were diluted and the virus was titered by a plaque assay and compared with the number of plaques in a control sample that was not exposed to light. The ratio of the titer of the control sample to the titer of virus in each of the treated samples, is a measure of viral inactivation. The $log_{10}$ of this ratio is herein called $log_{10}$ inactivation.

The results are shown in FIG. 1 in which the log of the Φ6 inactivation is plotted versus the negative log of the concentration of methylene blue. The optimal concentration of methylene blue for maximal virus inactivation is about 5 μM.

EXAMPLE 2

Forty μl bacteriophage Φ6 and 7.5 μl of 1 mg/ml methylene blue were added to 4 ml samples containing varying concentrations of plasma in Unisol. The concentrations of plasma varied between 2.5% and 100%. The final concentration of methylene blue in each sample was 5 μM. The control sample contained bacteriophage, methylene blue and 100% plasma.

Each sample, except for the control, was exposed to a fluence rate of 2 $mW/cm^2$ of the light delivered by General Electric F15T8-R bulbs for 5 minutes. The virus in each sample was titered and the results are set forth in TABLE 2. It can be seen that the method was effective in inactivating virus in plasma at all concentrations, including concentrations of 16% and higher.

Figure 2:
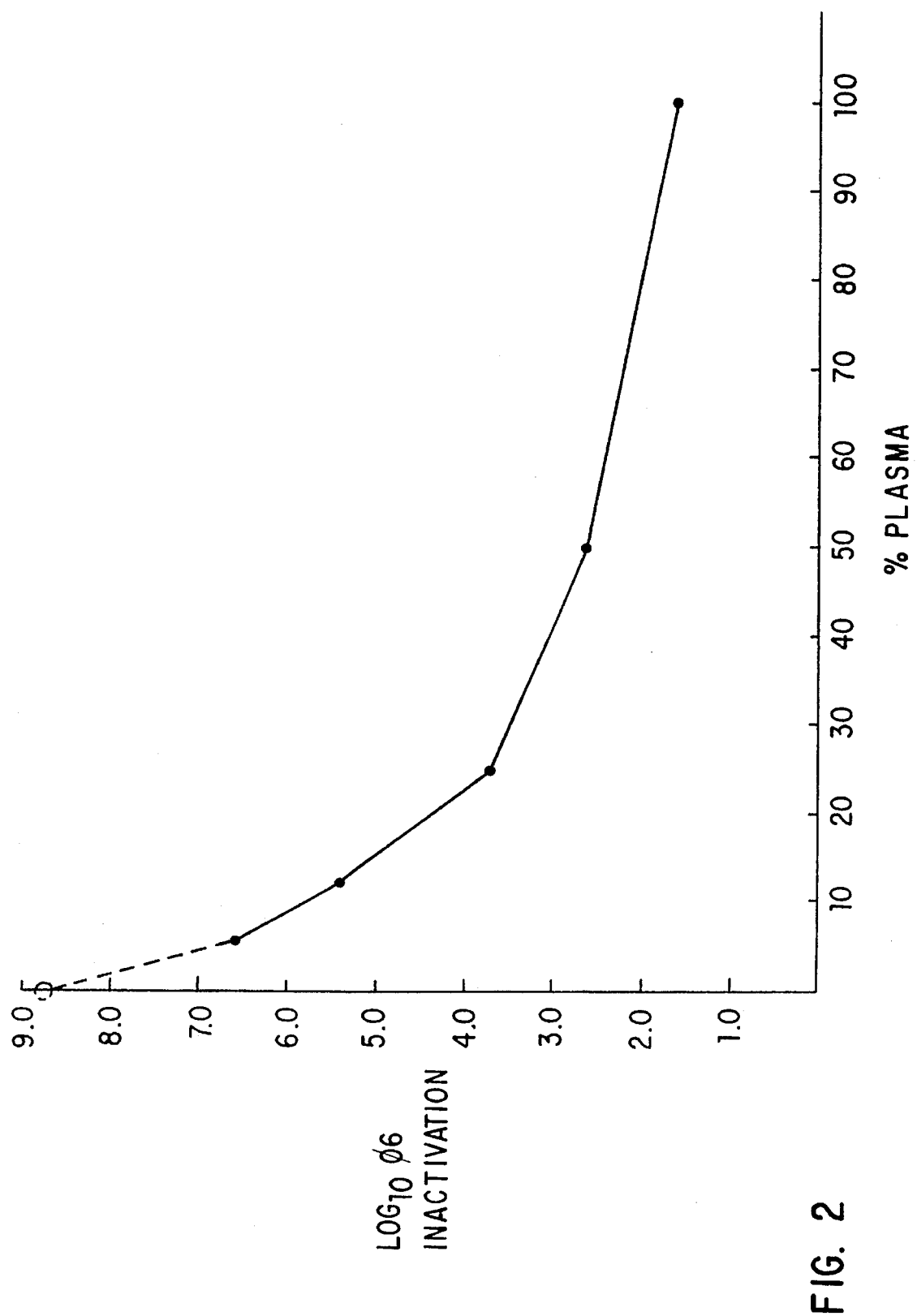
FIG. 2 presents the dependence of the inactivation of bacteriophage Φ6 by 40 μg/ml amino-methyl-trimethyl psoralen (AMT) as a function of plasma concentration in Unisol. Samples containing the bacteriophage, AMT, and increasing concentrations of plasma were exposed to UVA irradiation (wavelength of 365 nm) at a fluence rate of 42 mW/cm$^2$ for 90 seconds.

In contrast to the results set forth in TABLE 2, when viral inactivation using other dyes, including MC 540, various psoralens, and various porphyrins, was measured, inactivation was significantly reduced (up to $10^5$) as a function of increasing plasma concentration (see FIG. 2 and TABLE 3).

In FIG. 2, bacteriophage Φ6 was added to increasing amounts of plasma. Forty μg/ml of amino-methyl-trimethyl psoralen (AMT) was added to the plasma-bacteriophage mixture and irradiated with UVA light (wavelength of 365 nm) at a fluence rate of 42 $mW/cm^2$ for 90 seconds.

TABLE 3 presents the results of experiments in which increasing concentrations of plasma were inoculated with VSV and treated with 6.25 μM MC 540 and visible light for 60 minutes. As with bacteriophage Φ6 and AMT (FIG. 2), MC 540 is unsuitable for decontaminating blood components that contain high levels of plasma.

As plasma concentration increases, the degree of viral inactivation decreases significantly, which indicates that dyes, other than phenothiazin-5-ium dyes, are unsuitable for decontaminating blood components. Thus, unlike most dyes and photosensitizing compounds, phenothiazin-5-ium dyes are able to decontaminate high concentrations of plasma.

The ineffectiveness of treatment using other dyes is most likely the result of binding of the dye to proteins and other plasma constituents so that at higher plasma concentrations virus inactivation is competitively inhibited. Surprisingly, however, this does not occur with the phenothiazin-5-ium dyes sufficiently to interfere with viral inactivation or, as demonstrated, infra., to substantially harm or alter cellular blood components.

TABLE 2

PLASMA INDEPENDENCE OF INACTIVATION OF BACTERIOPHAGE Φ6 BY METHYLENE BLUE

| Plasma Concentration (%) | Titer | $log_{10}$ inactivation |
|---|---|---|
| 100, control | $3.4 \times 10^8$ | — |
| 2.5 | $2.6 \times 10^2$ | 6.1 |
| 16 | $9.9 \times 10^2$ | 5.5 |
| 30 | $1.2 \times 10^3$ | 5.5 |
| 50 | $5.7 \times 10^2$ | 5.8 |
| 100 | $1.2 \times 10^3$ | 5.5 |

Control = no light treatment

TABLE 3

PLASMA DEPENDENCE OF INACTIVATION OF VSV BY MEROCYANINE 540

| Plasma Concentration (%) | Titer | $log_{10}$ inactivation |
|---|---|---|
| Controls: | | |
| Mock Infection | 0 | — |
| Virus Control | $5 \times 10^8$ | — |
| Virus in 100% Plasma | $2.4 \times 10^8$ | — |

TABLE 3-continued

PLASMA DEPENDENCE OF INACTIVATION OF VSV BY MEROCYANINE 540

| Plasma Concentration (%) | Titer | $\log_{10}$ inactivation |
|---|---|---|
| Virus Treated: | | |
| 0% Plasma | $<8.0 \times 10^1$ | $>6.4$ |
| 6.25% Plasma | $<8.0 \times 10^1$ | $>6.4$ |
| 12.5% Plasma | $1.6 \times 10^4$ | 4.1 |
| 25% Plasma | $4.5 \times 10^6$ | 1.8 |
| 50% Plasma | $1.5 \times 10^7$ | 1.1 |
| 100% Plasma | $1.0 \times 10^8$ | 0.1 |

Virus: Vesicular Stomatitis Virus (VSV)
Assay: Plaque counts (agarose overlay) on BGMK cells
Treatment: 6.25 µM MC 540, 60 minutes visible light

EXAMPLE 3

Red cells were prepared by centrifugation of whole blood to form packed red cells. The supernatant was expressed off. The remaining red cell pellet had a hematocrit of 85–95% (volume percent occupied by red cells).

In this instance, packed red cells were diluted with 0.9% saline to a hematocrit of 55% and then the red cells were leukocyte-depleted by filtration through a three log filter that decreases their concentration by a factor of $10^3$. Aliquots of the red cells were diluted with ARC 8 to final hematocrits of 15 or 30% and contained about 2.5% plasma.

Forty µl of bacteriophage Φ6 and varying amounts of 1 mg/ml methylene blue were added to 4 ml samples of the leukocyte-depleted red cells, which were at a hematocrit of 15 or 30%. Methylene blue was added to each sample, except for the control, at final concentrations of 1, 5, or 25 µM. The samples were then exposed to light, as described in Example 2 for different lengths of time and the titer of the virus was assayed. The results of this experiment are summarized in TABLE 4.

The experiment was also performed with a red blood cell sample at a hematocrit of 55% with 5 µM methylene blue and 60 minutes of light exposure at a fluence rate of 0.8 mW/cm². The sample, however, was placed on a reciprocating shaker during exposure to the light. The $\log_{10}$ inactivation was 5.7.

TABLE 4

INACTIVATION OF BACTERIOPHAGE Φ6 IN RED CELLS

| Sample | Titer | $\log_{10}$ Inactivation |
|---|---|---|
| Hematocrit 15%: | | |
| Control, no MB no light | $3.1 \times 10^8$ | — |
| Control, 25 µM MB, no light | $3.4 \times 10^8$ | 0.0 |
| Control, no MB 16 m. light | $2.3 \times 10^8$ | 0.1 |
| 25 µM + 5 m. lt. | 10 | 7.5 |
| 5 µM + 5 m. lt. | $5.9 \times 10^2$ | 5.7 |
| 5 µM + 15 m. lt. | <10 | >7.5 |
| 1 µM + 5 m. lt. | $4.7 \times 10^7$ | 0.8 |
| 1 µM + 15 m. lt. | $4.2 \times 10^2$ | 5.9 |
| 1 µM + 25 m. lt. | $3.0 \times 10^1$ | 7.2 |
| Hematocrit 30%: | | |
| 5 µM + 5 m. lt. | $2.0 \times 10^8$ | 0.2 |
| 5 µM + 15 m. lt. | $1.1 \times 10^8$ | 0.5 |

TABLE 4-continued

INACTIVATION OF BACTERIOPHAGE Φ6 IN RED CELLS

| Sample | Titer | $\log_{10}$ Inactivation |
|---|---|---|
| 5 µM + 25 m. lt. Hematocrit 55%: | $3.6 \times 10^4$ | 3.9 |
| 5 µM + 30 m. lt. + shaking | $6 \times 10^2$ | 5.7 |

"MB", "m" and "m. lt." mean methylene blue, minutes and minutes of light, respectively.

TABLE 5

INACTRVATION OF VSV IN 16% PLASMA BY METHYLENE BLUE

| Sample | Titer | $\log_{10}$ inactivation |
|---|---|---|
| Control: | | |
| no dye | $1.5 \times 10^8$ | — |
| no light | $2.3 \times 10^7$ | 0.8 |
| 15 s. lt. | $4.2 \times 10^5$ | 2.6 |
| 30 s. lt. | $1.4 \times 10^4$ | 4.0 |
| 60 s. lt. | $<8 \times 10^1$ | >6.3 |

25 µM Methylene Blue
Fluence rate: 2 mW/cm² delivered by General Electric F15T8-R fluorescent bulbs
s. lt. means seconds of light.

EXAMPLE 4

The inactivation of VSV in 4 ml samples of 16% plasma/ Unisol by 25 µM methylene blue as a function of time of light exposure was measured. The results are set forth in TABLE 5. VSV is rapidly inactivated in plasma by light plus methylene blue.

EXAMPLE 5

The inactivation of bacteriophage Φ6 in platelet concentrates (PC) and in leukodepleted platelet concentrates (LDPC) was studied. Platelet concentrates contain about $2 \times 10^8$ platelets per ml. The concentrates are depleted of leukocytes by filtration as described in Example 3 to produce LDPC.

Forty µl of bacteriophage Φ6 was added to 4 ml samples of either PC or LDPC, which contained 5 µM methylene blue. The control sample was not exposed to light and the other samples were either exposed to light for 5 minutes or 25 minutes. The results are set forth in TABLE 6.

The data in TABLE 6 indicate that viral inactivation is somewhat slower in the presence of leukocytes than in their absence. The presence of leukocytes appears to interfere with the inactivation of viral contaminants in PC so that longer light exposure or higher concentrations of dye were needed to achieve inactivation. The reason for this interference was not clear.

In order to ascertain whether methylene blue binds to or is otherwise taken up by leukocytes, leukocytes from the buffy coat were incubated in the presence of methylene blue. After incubation the leukocytes were spun down and the concentration of methylene blue in the supernatant was compared to the concentration of methylene blue in the absence of leukocytes. There was no difference in the concentration of methylene blue, which indicated that, although leukocytes contain DNA, they do not bind or take up methylene blue.

In contrast, when a similar experiment was conducted with red blood cells, the concentration of methylene blue in the supernatant was substantially less than the initial concentration of methylene blue before the addition of red blood cells. This indicated that red blood cells take up or bind methylene blue so that the experiment with leukocytes should have detected any dye uptake or binding by leukocytes.

EXAMPLE 6

The inactivation of bacteriophage Φ6 in 16% plasma by 5 μM toluidine blue O, another phenothiazin-5-ium dye, as a function of exposure to light was examined. The results, which are set forth in TABLE 7, indicated that toluidine blue O is as effective as methylene blue for the inactivation of bacteriophage Φ6 in plasma.

TABLE 6

INACTIVATION OF BACTERIOPHAGE Φ6 IN PLATELET CONCENTRATES

| Sample | Titer | $\log_{10}$ inactivation |
|---|---|---|
| Control | $1.6 \times 10^8$ | — |
| 5 m. lt. (PC) | $1.1 \times 10^5$ | 3.2 |
| 5 m. lt. (LDPC) | $4.5 \times 10^2$ | 5.6 |
| 25 m. lt. (PC) | $8.2 \times 10^1$ | 6.3 |
| 25 m. lt. (LDPC) | $1.1 \times 10^1$ | 7.2 |

5 μM Methylene Blue
Fluence rate: 2 mW/cm² delivered by General Electric F15T8-R fluorescent bulbs
PC: platelet concentrate
LDPC: leukodepleted platelet concentrate
m. lt.: minutes of light

TABLE 7

INACTIVATION OF BACTERIOPHAGE Φ6 IN 16% PLASMA BY TOLUIDINE BLUE O

| Sample | Titer | $\log_{10}$ inactivation |
|---|---|---|
| Control: | | |
| no light | $1.6 \times 10^8$ | — |
| 1 min. lt. | $4.3 \times 10^3$ | 4.6 |
| 2 min. lt. | $5.5 \times 10^1$ | 6.5 |
| 4 min. lt. | $2 \times 10^0$ | 7.9 |

5 μM Toluidine Blue O
Fluence rate: 2 mW/cm² delivered by General Electric F15T8-R fluorescent bulbs.

EXAMPLE 7

Since blood for transfusion is generally collected and stored in blood bags, the inactivation of bacteriophage Φ6 by methylene blue in red blood cells in bags was studied. Gas permeable bags were filled with a sufficient amount of red blood cell solution to fill them to a thickness of 4 mm. A parallel experiment was conducted with red blood cells at a thickness of 4 mm in petri dishes. The results of these experiments are set forth in TABLE 8.

The blood bags were filled with 62 ml of red blood cells, which had been leukodepleted with a 5 log filter, diluted to a hematocrit of 30%, and inoculated with bacteriophage Φ6 as in the previous Examples. In order to prevent any decrease in the light intensity over the length of the bags, they were sealed with hemostats, rather than relying on the ports, which would have blocked light flux. Samples were extracted with a needle through the side of the bags.

As indicated in TABLE 8, treatment with methylene blue and light in the gas permeable bags inactivated the phage.

EXAMPLE 8

The ability of the phenothiazin-5-ium dye, thionine, to inactivate bacteriophage Φ6 in 100% plasma in the presence of red light was studied. From the results, which are set forth in TABLE 9, it was concluded that thionine is effective for decontaminating whole blood and blood components.

TABLE 8

INACTIVATION OF BACTERIOPHAGE Φ6 IN RED BLOOD CELLS IN BLOOD BAGS AND PETRI DISHES BY METHYLENE BLUE

| Sample | Titer | $\log_{10}$ inactivation |
|---|---|---|
| Petri dish: | | |
| no light | $8.9 \times 10^8$ | — |
| 30 min. lt. | $1.6 \times 10^3$ | 5.7 |
| 60 min. lt. | $2.7 \times 10^2$ | 6.5 |
| Bag: | | |
| no light | $1.1 \times 10^9$ | — |
| 30 min. lt. | $3.7 \times 10^6$ | 2.5 |
| 60 min. lt. | $3.5 \times 10^4$ | 4.5 |
| 90 min. lt. | $1.8 \times 10^3$ | 5.8 |
| 120 min. lt. | $1.8 \times 10^2$ | 5.8 |

5 μM Methylene blue
Gas permeable blood preservation bags were used.
Fluence rate: 0.8 mW/cm² delivered by General Electric F40T8-R bulbs
Red blood cells were leukodepleted with a 5 log filter and suspended at a hematocrit of 30% in ARC 8.
min. lt. means minutes of light.

TABLE 9

INACTIVATION OF BACTERIOPHAGE Φ6 IN 100% PLASMA BY THIONINE AND RED LIGHT

| Sample | Titer | $\log_{10}$ inactivation |
|---|---|---|
| no light | $4.4 \times 10^8$ | — |
| 2 min. lt. | $3.9 \times 10^5$ | 3.1 |
| 4 min. lt. | $3.8 \times 10^4$ | 4.1 |
| 8 min. lt. | $2.5 \times 10^3$ | 5.2 |
| 16 min. lt. | $4.1 \times 10^2$ | 6.0 |

5 μM Thionine
Fluence rate: 0.8 mW/cm²
min. lt. means minutes of light.

EXAMPLE 9

The inactivation of VSV in red blood cells by methylene blue and light was examined. Samples of red blood cells, which had been leukodepleted with a 5 log filter and suspended at a hematocrit of 30% in ARC 8, were inoculated with VSV and were treated with methylene blue at a concentration of 5 μM. The samples were treated with red light as set forth in TABLE 10. The results of this experiment indicated that VSV in red blood cells was readily inactivated by methylene blue and light.

EXAMPLE 10

The effect of treatment with methylene blue and light on red blood cells was studied. The results of this experiment are set forth in TABLE 11.

Red blood cells were leukodepleted with a 5 log filter and suspended at a hematocrit of 30% in ARC 8.

TABLE 10

INACTIVATION OF VSV IN RED BLOOD CELLS
BY METHYLENE BLUE AND RED LIGHT

| Sample | Titer | $\log_{10}$ inactivation |
|---|---|---|
| no light | $1.2 \times 10^6$ | — |
| 15 min. lt. | $1.1 \times 10^4$ | 1.9 |
| 30 min. lt. | $8 \times 10^1$ | 4.1 |
| 60 min. lt. | $1 \times 10^0$ | 6.0 |
| 90 min. lt. | no plaques | $\geq 6.1$ |
| 120 min. lt. | no plaques | $\geq 6.1$ |

5 µM Methylene blue
Fluence rate: 0.8 mW/cm² delivered by General Electric F40T8-R bulbs
Red blood cells were leukodepleted with a 5 log filter and suspended at a hematocrit of 30% in ARC 8.
VSV means Vesicular Stomatitis Virus.
min. lt. means minutes of light.

TABLE 11

RED CELL VIABILITY AFTER TREATMENT
WITH 5 µM METHYLENE BLUE AND
90 MINUTES OF LIGHT

| Sample | % Hem | ATP µM/g Hgb | 3-DPG µM/g Hgb | EC* pH | Morph Score |
|---|---|---|---|---|---|
| C - 0 | 0.24 | 5.8 | 12.9 | 7.10 | 98.8 |
| T - 0 | 0.23 | 6.1 | 13.0 | 7.10 | 98.0 |
| C - 7 | 0.36 | 7.4 | 16.5 | 7.11 | 81.2 |
| T - 7 | 0.42 | 7.8 | 13.7 | 7.08 | 82.7 |
| C - 14 | 0.38 | 7.9 | 18.6 | 7.06 | 84.3 |
| T - 14 | 0.46 | 7.4 | 14.6 | 7.05 | 81.9 |
| C - 23 | 0.53 | 7.4 | 21.1 | 6.83 | — |
| T - 23 | 0.71 | 6.1 | 18.0 | 6.90 | — |
| C - 28 | 0.53 | 7.4 | 24.4 | 6.67 | 79.7** |
| T - 28 | 0.73 | 6.4 | 16.2 | 6.75 | 79.5** |
| C - 36 | 0.82 | 6.0 | 21.2 | 6.64 | 77.2 |
| T - 36 | 1.11 | 5.5 | 12.1 | 6.71 | 78.8 |
| C - 42 | 0.96 | 8.5 | 25.4 | 6.57 | 77.2 |
| T - 42 | 1.40 | 7.1 | 14.5 | 6.61 | 79.6 |

Fluence rate: 0.8 mW/cm² delivered by General Electric F40T8-R bulbs
Red blood cells were leukodepleted with a 5 log filter and suspended at a hematocrit of 30% in ARC 8.
C - n = control red blood cells stored for "n" days.
T - n = treated red blood cells stored for "n" days.
*EC = extracellular
**assessed on day 30
Hem means hematocrit.
Morph means morphology.

Sixty-two ml were introduced into a blood bag as described in Example 7 and the blood bag was stored at 4° C. At the times indicated in TABLE 11, samples were removed from the bag with a needle and the in vitro properties of the cells were assessed. A second 62 ml sample of cells was introduced into a blood bag and stored at 4° C. This second bag was the control.

The in vitro properties that were measured included: extracellular pH; percentage of hemolysis; the concentrations of ATP and 2,3 DPG; and morphology. The in vitro properties of the treated and untreated samples were measured and compared to ascertain the effects, if any, of light and methylene blue on stored red blood cells.

The results, which are set forth in TABLE 11, indicated that treatment with methylene blue and light did not have a substantial effect on red cells. Thus, red cells that have been decontaminated with methylene blue and light can be used for transfusion. Further, red cells that have been treated and then stored for extended periods of time remain suitable for transfusion.

EXAMPLE 11

Figure 3:
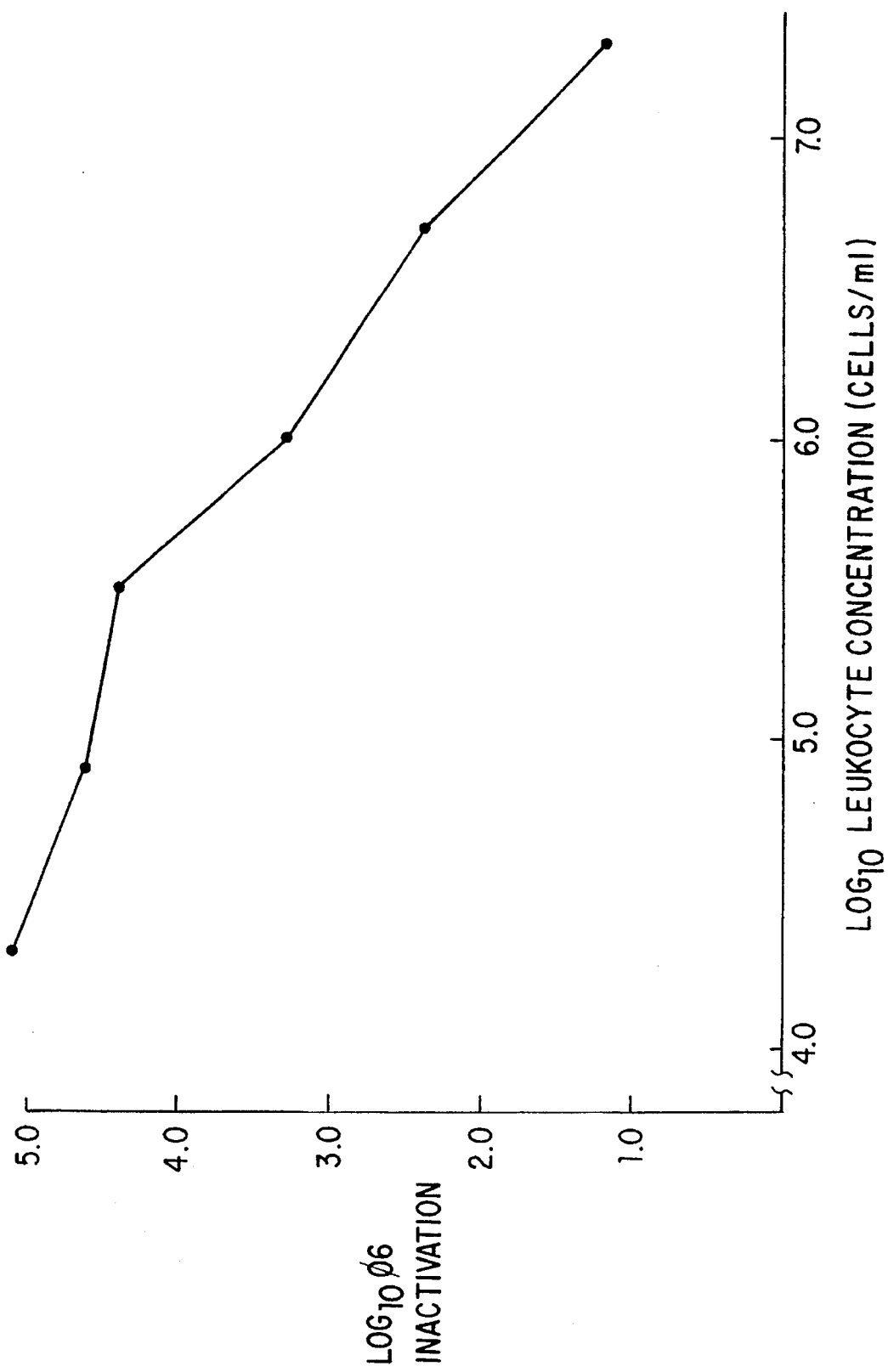
FIG. 3 depicts the dependence of bacteriophage Φ6 inactivation in platelet concentrates as a function of leukocyte concentration. Increasing concentrations of leukocytes were added to 4 ml samples of three log leukocyte-depleted platelet concentrates which contained about 2×10$^8$ platelets per ml. Five μM methylene blue was added to each sample which was then exposed for 5 minutes to light at a fluence rate of 2 mW/cm$^2$ of sample delivered by General Electric F15T8-R bulbs.

A platelet concentrate in 16% plasma/Unisol was leukodepleted with a three log filter. Starting at a concentration of $2 \times 10^8$/ml, serial 4-fold dilutions of the leukocytes were prepared. Two and 7/10ths (2.7) ml samples of the platelet concentrate were added to 300 µl of the dilutions. Bacteriophage stock was added as in the previous Examples. Methylene blue was then added to each sample to a final concentration of 5 µM. Each sample was irradiated for 5 minutes with light having a fluence rate of 2 mW/cm². The results are shown in FIG. 3 from which it can be concluded that the presence of leukocytes inhibits viral inactivation by methylene blue.

Since modifications will be apparent to those of skill in the art, it is intended that this invention be limited only by the scope of the appended claims.

EXAMPLE 12

INACTIVATION OF VSV IN PLATELET
CONCENTRATES BY METHYLENE BLUE AND
RED LIGHT

A platelet concentrate in 100% plasma was leukodepleted with a three log Pall PL50 filter. Unfiltered platelet concentrate was retained as a control. VSV stock was added as in the previous Examples. Methylene blue was then added to each sample to a final concentration of 1 µM. Each sample was irradiated with light having a fluence rate of 0.8 mW/cm² that was produced by GE F40T8-R bulbs. The results demonstrated that the technique inactivated VSV in leukodepleted platelet concentrates (Table 11).

TABLE 11

INACTIVATION OF VSV IN PLATELET
CONCENTRATES BY METHYLENE
BLUE AND RED LIGHT

| | $\log_{10}$ VSV Inactivation | |
|---|---|---|
| Red Light Exposure (minutes) | Unfiltered Platelet Concentrates | Leukocyte Depleted Platelet Concentrates |
| 0 | 0.0 | 0.0 |
| 30 | 2.2 | 3.1 |
| 60 | 2.6 | 4.1 |
| 90 | 2.9 | 4.5 |
| 120 | 2.8 | 5.4 |

Methylene blue concentration: 1 µM
Fluence rate: 0.8 mW/cm² delivered by General Electric F40T8-R bulbs

EXAMPLE 13

IN VITRO PROPERTIES OF LEUKODEPLETED,
FILTERED PLATELET CONCENTRATES
TREATED WITH METHYLENE BLUE AND
RED LIGHT

Three platelet concentrates (100% plasma, identical ABO type) were pooled, were leukodepleted with a three log Pall PL50 filter, and were divided into three units. Methylene blue (final concentration, 1 μM) was added to two of the units on day 0. One unit was retained as a control. The methylene blue-containing samples were irradiated for 30 or 120 minutes with red light (fluence rate, 0.8 mW/cm$^2$). Control and treated units were stored under typical blood bank conditions (22° C. with agitation). Morphology score was determined microscopically on 100 platelets. A perfect disk scored 4 points, an altered disk shape scored 3 points, spheres scored 2 points, dendritic shapes scored 1 point, and balloon shapes scored 0 points. Therefore, a maximum score for 100 platelets, each scored as a disk, would be 400. The results indicate that no significant alteration of platelet properties occurred in vitro for methylene blue-treated samples which were irradiated for 30 minutes compared to untreated controls through 5 days of storage (Table 12). Samples irradiated for 120 minutes had some alterations in platelet properties in vitro.

TABLE 13

INACTIVATION OF BACTERIOPHAGE Φ6 BY METHYLENE BLUE AND RED LIGHT IN WHOLE BLOOD

| Methylene Blue Concentration (μM) | RUN 1 (43% Hct) log$_{10}$ inact. | RUN 2 (38% Hct) log$_{10}$ inact. |
|---|---|---|
| 5 | 2.0 | 1.0 |
| 10 | 3.8 | 1.3 |
| 15 | 4.2 | 2.5 |
| 20 | 4.5 | 2.9 |

TABLE 12

IN VITRO PROPERTIES OF LEUKODEPLETED, FILTERED PLATELET CONCENTRATES TREATED WITH METHYLENE BLUE AND RED LIGHT

| In Vitro Properties | Day 1 | | | Day 5 | | | RUN |
|---|---|---|---|---|---|---|---|
| | Control | 30 min.* | 120 min.* | Control | 30 min.* | 120 min.* | |
| pH | 7.45 | 7.42 | 7.40 | 7.36 | 7.35 | 7.28 | #1 |
|    | 7.38 | 7.37 | 7.34 | 7.36 | 7.27 | 7.19 | #2 |
| $\bar{X}$ | 7.42 | 7.40 | 7.37 | 7.36 | 7.31 | 7.24 | $\bar{X}$ |
| Platelet | 1.31 | 1.33 | 1.35 | 1.13 | 1.07 | 1.04 | #1 |
| Count | 1.27 | 1.31 | 1.39 | 1.25 | 1.14 | 1.07 | #2 |
| $\bar{X}$ | 1.29 | 1.32 | 1.37 | 1.19 | 1.11 | 1.06 | $\bar{X}$ |
| Morph. | 335 | 310 | 261 | 274 | 276 | 254 | #1 |
| Score | 315 | 319 | 282 | 252 | 237 | 150 | #2 |
| $\bar{X}$ | 325 | 315 | 272 | 263 | 257 | 202 | $\bar{X}$ |
| Aggra- | 6.5 | 5.5 | 4.5 | 4.0 | 4.0 | 4.0 | #1 |
| gation | 4.5 | 4.5 | 3.0 | 3.0 | 2.0 | 1.0 | #2 |
| Score | | | | | | | |
| $\bar{X}$ | 5.5 | 5.0 | 3.8 | 3.5 | 3.0 | 2.5 | $\bar{X}$ |
| HSR | 70 | 65 | 50 | 57 | 48 | 48 | #1 |
|     | 64 | 42 | 40 | 50 | 43 | 60 | #2 |
| $\bar{X}$ | 67 | 54 | 45 | 54 | 46 | 54 | $\bar{X}$ |

Methylene blue concentration: 1 μM
Fluence rate: 0.8 mW/cm$^2$ delivered by General Electric F40T8-R bulbs
HSR: Hypotonic shock response
Morph. Score = Morphological score
*irradiation time with red light

EXAMPLE 14

INACTIVATION OF BACTERIOPHAGE Φ6 BY METHYLENE BLUE AND RED LIGHT IN WHOLE BLOOD

Bacteriophage φ6 was added to whole blood. Methylene blue was then added at various concentrations. The samples were agitated at room temperature for 15 minutes prior to exposure to GE F20T12-R lamps (fluence=3.9 J/cm$^2$). The results demonstrated that methylene blue plus red light inactivated Φ6 in whole blood (Table 13).

EXAMPLE 15

INACTIVATION OF Φ6 BY METHYLENE BLUE AND LIGHT: 4° C. VS ROOM TEMPERATURE

A packed red cell unit was diluted to 55% Hct with saline, and was leukodepleted using a RC50 Pall filter. It was then further diluted to 30% Hct with ARC-8. Following spiking with bacteriophage φ6, methylene blue was added to a final concentration of 5 μM. Samples were agitated for 15 minutes at the indicated temperatures prior to exposure to one bank of GE fluorescent red lamps (F20T12-R, fluence rate= 0.75 mW/cm$^2$). Some sample-containing petri dishes were placed on ice which limited their reception of the light to only that produced by the light bank above instead of light from the two light banks. New fluorescent bulbs (F20T12-R) were employed for this study which have a higher fluence rate (0.75 mW/cm$^2$/light bank) than older lamps of the same type (0.4 mW/cm$^2$/light bank). The data demonstrated that inactivation of bacteriophage φ6 by light and methylene blue was more complete at 4° C. than at room temperature (Table 14).

TABLE 14

INACTIVATION OF Φ6 BY METHYLENE BLUE AND LIGHT:
4° C. VS ROOM TEMPERATURE

| | $\log_{10}$ inactivation | | | | | | | | | | | |
|---|---|---|---|---|---|---|---|---|---|---|---|---|
| | Run 1 | | Run 2 | | Run 3 | | Run 4 | | Run 5 | | $\bar{X}$ | |
| J/cm² | 4° C. | RT | 4° C. | RT | 4° C. | RT | 4° C. | RT | 4° C. | RT | 4° C. | RT |
| 0.0 | 0.0 | 0.0 | 0.0 | 0.0 | 0.0 | 0.0 | 0.0 | 0.0 | 0.0 | 0.0 | 0.0 | 0.0 |
| 1.3 | 1.8 | 1.1 | 5.0 | 1.5 | 4.6 | 3.6 | 1.3 | 1.2 | 4.8 | 1.9 | 3.5 | 1.9 |
| 3.9 | 5.3 | 2.9 | >7.7 | 3.1 | 7.1 | 5.8 | 4.6 | 4.3 | 6.0 | 3.8 | 6.1 | 4.0 |

EXAMPLE 16

COMPARISON OF BACTERIOPHAGE Φ6 INACTIVATION IN RED CELL SUSPENSIONS CONTAINING ADSOL OR ARC-8

Packed red cells were diluted to 55% Hct with saline, were leukodepleted with an RC50 Pall filter, and then were further diluted to 30% Hct with ADSOL or ARC-8. Bacteriophage φ6 and methylene blue were added to the samples as previously described. The final methylene blue concentration was 5 µM. The samples were agitated at room temperature for 15 minutes prior to exposure to red light produced by GE F20T12-R fluorescent lamps (2 banks, fluence rate=0.75 mW/cm²/light bank). New fluorescent bulbs were employed for this study which have a higher fluence rate (0.75 mW/cm²/light bank) than older lamps of the same type (0.4 mW/cm²/light bank). The data demonstrated that the inactivation of bacteriophage φ6 was greater in ARC-8 than in ADSOL (Table 15).

TABLE 15

COMPARISON OF BACTERIOPHAGE Φ6 INACTIVATION IN RED CELL SUSPENSIONS CONTAINING ADSOL OR ARC-8

| FLUENCE | RUN 1 $\log_{10}$ inactivation | | RUN 2 $\log_{10}$ inactivation | | $\bar{X}$ $\log_{10}$ inactivation | |
|---|---|---|---|---|---|---|
| (J/cm²) | ADSOL | ARC-8 | ADSOL | ARC-8 | ADSOL | ARC-8 |
| 0 | 0.0 | 0.0 | 0.0 | 0.0 | 0.0 | 0.0 |
| 0.9 | 0.3 | 3.1 | 0.7 | 1.3 | 0.5 | 2.2 |
| 1.8 | 1.7 | 3.4 | 1.4 | 3.2 | 1.6 | 3.3 |
| 3.6 | 2.6 | 4.1 | 3.2 | 4.2 | 2.9 | 4.2 |
| 4.5 | 2.6 | 4.8 | 5.2 | 6.6 | 3.9 | 5.7 |

EXAMPLE 17

Pseudorabies virus, a DNA-containing virus, was inactivated using the method of this invention in 30% hematocrit, leukodepleted, red blood cell suspensions in ARC-8. The samples were prepared and treated in the same general manner as samples containing VSV were prepared and treated (see original Example 9, original page 31). The incubation time of the sample with MB was about 15 minutes. The fluence rate was 0.8 mW/cm² and was delivered by a General Electric F40T8-R bulb.

The results are set forth in the following Table.

INACTIVATION OF PSEUDORABIES VIRUS BY MB PLUS LIGHT

| | Sample Titer | $\log_{10}$ inactivation |
|---|---|---|
| No dye, no light | 6.2 × 10⁵ | — |
| 5 µM MB + 15 min light | 4.9 × 10⁴ | 1.1 |
| 5 µM MB + 30 min light | 4.7 × 10³ | 2.2 |
| 5 µM MB + 45 min light | 7.2 × 10² | 3.0 |
| 5 µM MB + 60 min light | <2 | >5.5 |
| 5 µM MB + 90 min light | <2 | >5.5 |

These data demonstrate that the method of this invention inactivates psuedorabies virus in leukodepleted, red blood cell suspensions.

EXAMPLE 18

Extracellular HIV-1, an RNA-containing, enveloped virus, was inactivated in leukodepleted, red cell suspensions using the method of this invention.

Packed red cells were prepared from units of whole blood collected in CPDA-1 containers (PL-146, Baxter Healthcare, Deerfield, Ill.) by the American Red Cross Blood Services, Greater Chesapeake and Potomac Region. Units typically were centrifuged at 1471×g for 5 minutes, and platelet-rich plasma and the buffy coat were removed. The packed red cells were diluted to 50% hematocrit (Hct) with ARC-8. The resulting red cell suspensions were leukodepleted by the use of a filter (RC50, Pall Biomedical, East Hills, N.Y.) and were further diluted to 30% Hct with ARC-8.

HIV-1 was added to 11 ml red cell samples in 85 mm diameter polystyrene culture dishes. The final titer of virus-spiked samples was approximately $8\times10^4$ plaque-forming units per ml (pfu/ml). This equals a 40-fold dilution from stock. Methylene blue (MB) was added from a 2.7 mmole/L stock to the red cell suspension to give a final concentration of 5 μmoles/L. The culture dishes were agitated at room temperature on a horizontal reciprocal shaker (70 cycles/min) for 15 minutes in the dark. The sample thickness, or optical pathlength, in the culture dishes was 1.9 mm.

Samples were irradiated with one of two in-house fabricated light sources. Samples were placed on an air-cooled, transparent plastic stage (agitated 70 cycles/min) and were positioned midway (6 cm apart) from each of 2 light banks that illuminated samples from above and below. Depending on the light source, each light bank contained either five or eight red fluorescent bulbs (F20T12-R General Electric, Circleville, Ohio) having an emission peak at approximately 650 nm (half-peak emission at approx. 630 and 700 nm). Approximately 65% of the bulbs' emissions overlapped the absorption spectra of MB. Each light bank provided a fluence rate ($J/cm^2$/sec) of either 0.65 (5 bulb/bank) or 1.15 (8 bulb/bank) measured at the sample surface. Since 2 light banks illuminated each sample, each sample received a fluence rate of either 1.30 $J/cm^2$/sec (5 bulb/banks) or 2.30 $J/cm^2$/sec (8 bulb/banks). When appropriate, equivalent fluences (fluence rate×time) were obtained from the two light sources by extending the irradiation time of samples in the light produced by the 5 bulb/bank light source by approximately 75%. Fluence rates were measured by an optical power meter (Model 371, United Detector Technology, Hawthorne, Calif.) equipped with a silicon diode detector and a radiometric filter (400–1000 nm, Model 115-9, UDT Instruments, Orlando, Fla.). In red cell ion permeability studies, four 11 ml irradiated samples were pooled and were introduced into a 150 ml PL-146 transfer pack (Fenwal Biotech, Round Lake, Ill.). They were subsequently stored in the dark at 4° C. During the course of the experiments, dark controls were shielded with black cloth (estimated fluence<300 $J/m^2$).

HIV-I was obtained from Universal Biotechnology Incorporated (Rockville, Md.). MT2 and H9 cells were obtained from the NIH AIDS Research and Reference Reagent Program (Ogden BioServices, Rockville, Md.) and were propagated in RPMI 1640 medium supplemented with 10% fetal bovine serum (FBS) and 2 mmole/L L-glutamine.

The HIV syncytial assay has been described (Harada et al., *Science* 229:563–566 (1985); copy enclosed). Briefly, serial 2× dilutions (6–8) of samples were made across 96-well microtiter plates. MT2 cells were then dispersed, resuspended, coated, and adjusted to a concentration of $2-3\times10^5$. Each microtiter plate well was seeded with 100 μl of the cell suspension and the plates were incubated at 37° C. in 5% $CO_2$/air. Although the plates were monitored for activity on days 2–4, the assay was typically scored on the fifth day by microscopic examination for the wells containing virus-induced cytopathic evidence of syncytial formation. $TCID_{50}$ calculations were performed.

Red cell storage studies on 44 ml samples stored in 150 ml PL-146 containers were performed. Extracellular potassium and sodium concentrations were measured by flame photometry (Model IL943, Allied Instrumentation Laboratory, Lexington, Mass.) and direct anti-human IgG tests were performed and scored (see, Walker, R. H., ed., *Technical Manual*, 10th Edition, American Assoc. Blood Banks, Arlington, Va., pp. 529, 563 and 564 (1990); copies enclosed).

Under conditions which inactivated approximately 4 $log_{10}$ of extracellular HIV (Table 16), only minor alterations of the red cell surface were observed.

TABLE 16

MB-PHOTOINACTIVATION OF EXTRACELLULAR HIV-1 IN LEUKODEPLETED, 30% HCT, RED CELLS[1]

| Fluence ($J/cm^2$) | Inactivation[2] ($log_{10}$) |
|---|---|
| 0.0 | 0.0 and 0.0 |
| 0.07 | 2.1 and 1.5 |
| 0.14 | >3.8 and 2.0 |
| 0.28 | >3.8 and 3.3 |
| 0.55 | >3.8 and >4.3 |

[1]The final concentration of MB was 5 μmole/L.
[2]The values are from two experiments which were conducted in blood derived from different donors. The symbol ">" indicates that no syncytium was observed in any, of the experimental wells. The subsequent number represents the $log_{10}$ inactivation if 1 syncytium per well had been observed.

The maintenance of red cell surface characteristics in direct agglutination tests (Table 17) is demonstrated by the low level of serum protein binding to phototreated red cells after their exposure to the method of this invention.

TABLE 17

DIRECT AGGLUTINATION TESTING OF MB-PHOTOTREATED RED CELLS

| Sample | Fluence ($J/cm^2$) | Experiment #1 | #2 | #3 |
|---|---|---|---|---|
| Dark Control | 0.0 | 0 | 0 | 0 |
| MB[1] | 0.6 | MA[2] | MA | 0 |
| MB[1] | 3.5 | 3[+3] | 1[+*] | 1[+*] |

[1]The final concentration of MB was 5 μmole/L.
[2]Microscopic agglutination (MA) was observed.
[3]Macroscopic agglutination was scored from 1[+] (weakest) to 4[+] (strongest).
*"1[+]" here means that the observed agglutination was intermediate between 1[+] and 2[+].

Based on the observations that 4% of all patients receiving high doses of the antibiotic cephalothin develop a positive direct agglutination test with no appreciable increase in red cell sequestration (Sass et al., *J. Lab. Clin. Med.* 69:447–455 (1969); copy enclosed), it is unlikely that the microscopic agglutination (MA) observed in some test results would negatively impact red cell survival. MA should also not interfere with the diagnosis of most antibody-mediated transfusion reactions.

Figure 4:
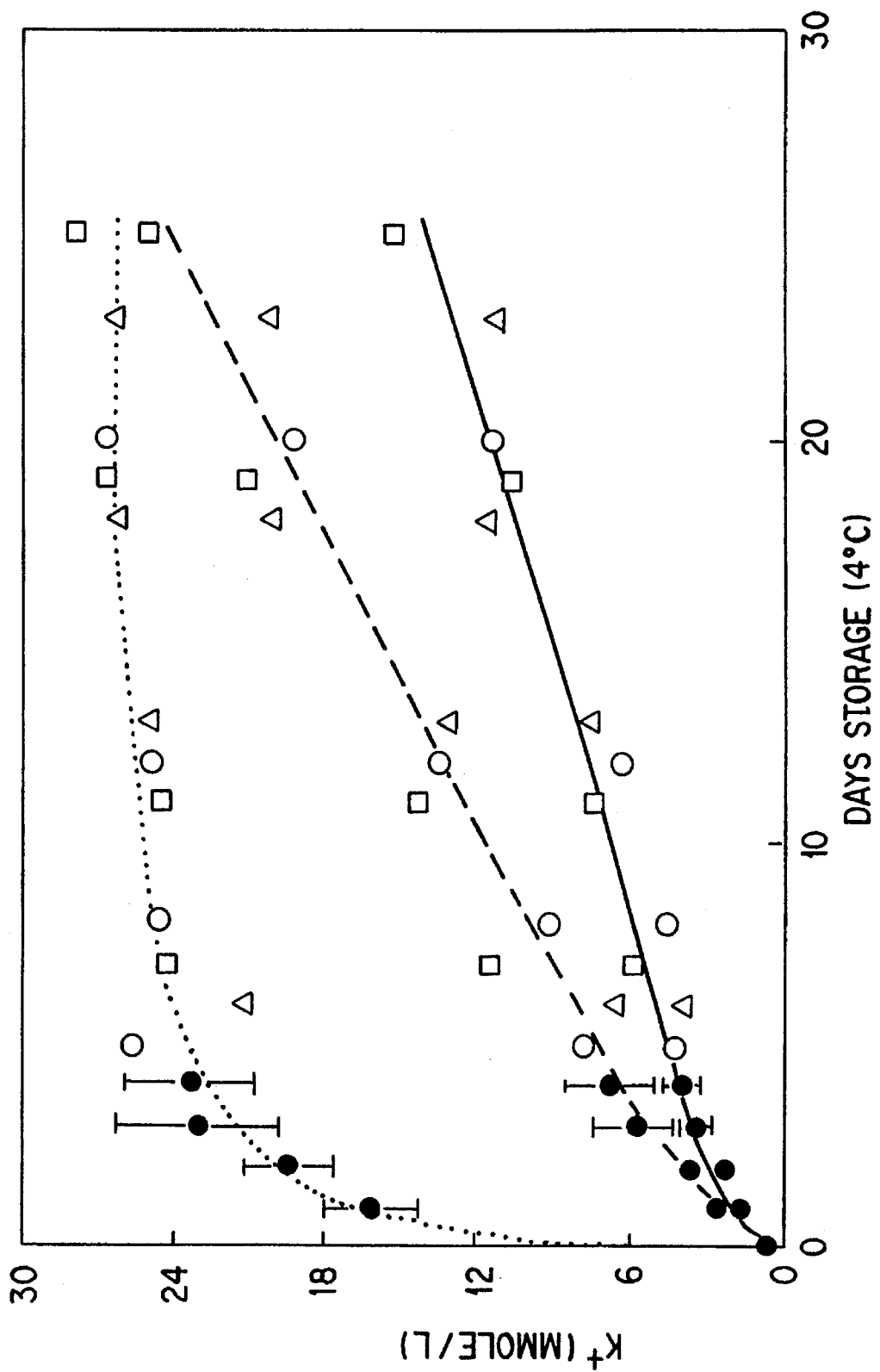
FIG. 4 depicts the leakage of potassium from methylene blue (MB)-phototreated red blood cells. The dotted line shows the potassium leakage from high fluence (3.5 J/cm$^2$) MB-treated red blood cells; the dashed line shows potassium flux from the low fluence (0.6 J/cm$^2$) MB-phototreated red blood cells; and the solid line shows the basal potassium leakage from untreated (no light) red blood cell controls. Each open symbol represents an experiment performed on red blood cells derived from a different individual; each closed symbol represents the average of data from three experiments. Error bars depict standard deviations.

Under conditions which inactivated approximately 4 $log_{10}$ of extracellular HIV-1 (Table 16), only a small increase (<2 fold) in red cell potassium efflux was observed over control levels (FIG. 4). This leakage rate is comparable to the modest potassium leakage (roughly 2 fold over rates from untreated controls) associated with routine gamma irradiation of red cells (Jeter et al., *Ann. Clin. Lab. Sci.* 21:177–186 (1991); copy enclosed).

FIG. 4 shows the leakage of potassium from MB-phototreated red cells. In FIG. 4, the dotted line shows the potassium leakage from high fluence (3.5 $J/cm^2$) MB-treated red cells. The dashed line shows potassium flux from the low fluence (0.6 $J/cm^2$) MB-phototreated red cells. The solid line shows the basal potassium leakage from untreated (no light) red cell controls. Each type of open symbol shows results from an experiment performed on red cells derived from a different individual. Closed symbols represent the average of data from three experiments. Error bars depict standard deviations. Low fluence MB treatment results in only a modest increase in potassium efflux from red cells compared to controls.

EXAMPLE 19

Intracellular HIV-1 was not inactivated using the method of this invention.

The HIV co-cultivation assay was based on the continuous production of HIV in H9 cells as described by Popovic et al. (*Science* 224:497–500 (1984); copy enclosed). H9 cells were prepared, pre-incubated for 30 minutes in medium containing 2 µg/ml polybrene (Sigma Chemical Company, St. Louis, Mo.), were centrifuged and resuspended in a small volume of fresh medium. They were then counted and their number was adjusted to yield a concentration of $1.2 \times 10^6$ cells/ml. The suspension was then added, at 0.5 ml/well, to the wells of cluster plates (Corning Glass Company, Corning, N.Y.) and an equal volume of control or treated HIV suspended in red cells was introduced. Infection was allowed to proceed for 1 hour at 37° C. after which the contents of each well were centrifuged through Ficol Hypaque (Sigma Chemical Company, St. Louis, Mo.) for removal of the red cells which would otherwise interfere with the assay. Approximately 0.4 ml H9 cells were recovered from this step and were added to the wells of new cluster plates containing 3.6 ml of fresh medium per well. New uninfected H9 cells were prepared, centrifuged, resuspended, counted, and adjusted to $2 \times 10^5$ cells/ml. One ml of H9-infected cells from each well was centrifuged and the pellets were resuspended in 1 ml of fresh uninfected H9 cells. The resulting cell suspension was added to the wells of new cluster plates containing 3 ml of fresh medium per well. Three to four days later, 1 ml of H9-infected cells were centrifuged and the pellets were resuspended in 1 ml of fleshly prepared uninfected H9 cells. The cell suspension was then added to the wells containing 3 ml of fresh medium. For subsequent passages, 3 ml of the cell suspension were removed from each well and were replaced with $2 \times 10^5$ uninfected H9 cells in 3 ml of medium. After the third and sixth passages, culture fluid was assayed by HIV p24 core profile ELISA (Dupont, Wilmington, Del.).

HIV-1-infected H9 cells were added to 11 ml red cell samples as before. Experiments involving the attempted inactivation of intracellular HIV-1 were carried out as described in paragraph 2 with the exception that H9 cells productively infected with HIV-1 were substituted for free virus. The final titer for H9-infected cells in red cell samples was approximately $2 \times 10^4$ infected cells/ml.

The plaque assay for animal viruses has been described (Dulbecco, R., *Proc. Natl. Acad. Sci. USA* 38:747–752 (1952); copy enclosed). Vero cells (ATCC CC181) were obtained from the American Type Culture Collection (ATCC), Rockville, Md. and were seeded into 6-well tissue culture plates (Corning Glass Company, Corning, N.Y.). They were allowed to grow to confluency and the monolayers were then infected in duplicate for each dilution. A 250 µl inoculum of phosphate buffered saline (PBS)-diluted or -undiluted sample was applied to the monolayer and infection was allowed to continue with intermittent rocking at 37° C. in 5% $CO_2$/air for 45 minutes. A 2 to 3 ml agarose overlay (2% agarose, 2% minimal essential medium without phenol red, 1:1 (Gibco/BRL, Gaithersburg, Md.)) was added and, after allowing the overlay to harden at room temperature, the microtiter plates were incubated at 37° C. in 5% $CO_2$/air overnight. All overlays were removed the following day; monolayers were fixed with 10% formaldehyde in PBS and were stained with 1% crystal violet (Sigma Chemical Company, St. Louis, Mo.) in methanol. Plaques were then counted manually.

MB phototreatment did not inactivate intracellular HIV-1 virus (data not shown). Therefore, it is likely that any virus inactivation procedure for red cells would need to be combined with a high efficiency ($\geq 6 \log_{10}$) leukocyte depletion. To Applicant's knowledge, no inactivation method for red cells exists which can inactivate the estimated 6 $\log_{10}$ of intracellular HIV virus load (Wagner et al., *Transfers. Med. Rev.* 5:18–32 (1991); copy enclosed) and maintain red cell properties (e.g., morphology, etc.) through a significant period of refrigerated storage (i.e., 35–42 days).

EXAMPLE 20

Extracellular Sindbis virus, an enveloped, RNA-containing virus, was inactivated in leukodepleted, red cell suspensions using the method of this invention. The general methods used have already been described in Example 18. The Sindbis virus was added to 4 ml red cell samples in 30 mm polystyrene culture dishes. The final titer of Sindbis virus-spiked samples was approximately $5 \times 10^5$ pfu/ml.

Sindbis virus (ATCC VR-68) was obtained from the ATCC (Rockville, Md.). Cells were propagated in McCoy's 5A medium supplemented with 10% FBS and 2 mmole/L L-glutamine (Gibco/BRL, Gaithersburg, Md.).

The plaque assay for animal viruses has been described previously (Dulbecco, R., *Proc. Natl. Acad. Sci. USA* 38:747–752 (1952)). Briefly, Vero cells were seeded into 6-well tissue culture plates (Corning Glass Company, Corning, N.Y.) and were allowed to grow to confluency. The monolayers were then infected in duplicate for each dilution. A 250-µl inoculum of PBS-diluted or -undiluted samples was applied and infection was allowed to continue with intermittent rocking at 37° C. in 5% $CO_2$/air for 45 minutes. A 2- to 3-ml agarose overlay (2% agarose, 2% minimal essential medium without phenol red, 1:1 (Gibco/BRL, Gaithersburg, Md.) was added. After allowing the overlay to harden at room temperature, the microtiter plates were incubated at 37° C. in 5-percent $CO_2$/air overnight. All overlays were removed the following day; monolayers were fixed with 10% formaldehyde in PBS and were stained with 1% crystal violet (Sigma Chemical Company, St. Louis, Mo.) in methanol. Plaques were then counted manually.

Under conditions which inactivated more than 5 $\log_{10}$ Sindbis virus (FIG. 5) only minor alterations of red cells were observed as previously described.

Figure 5:
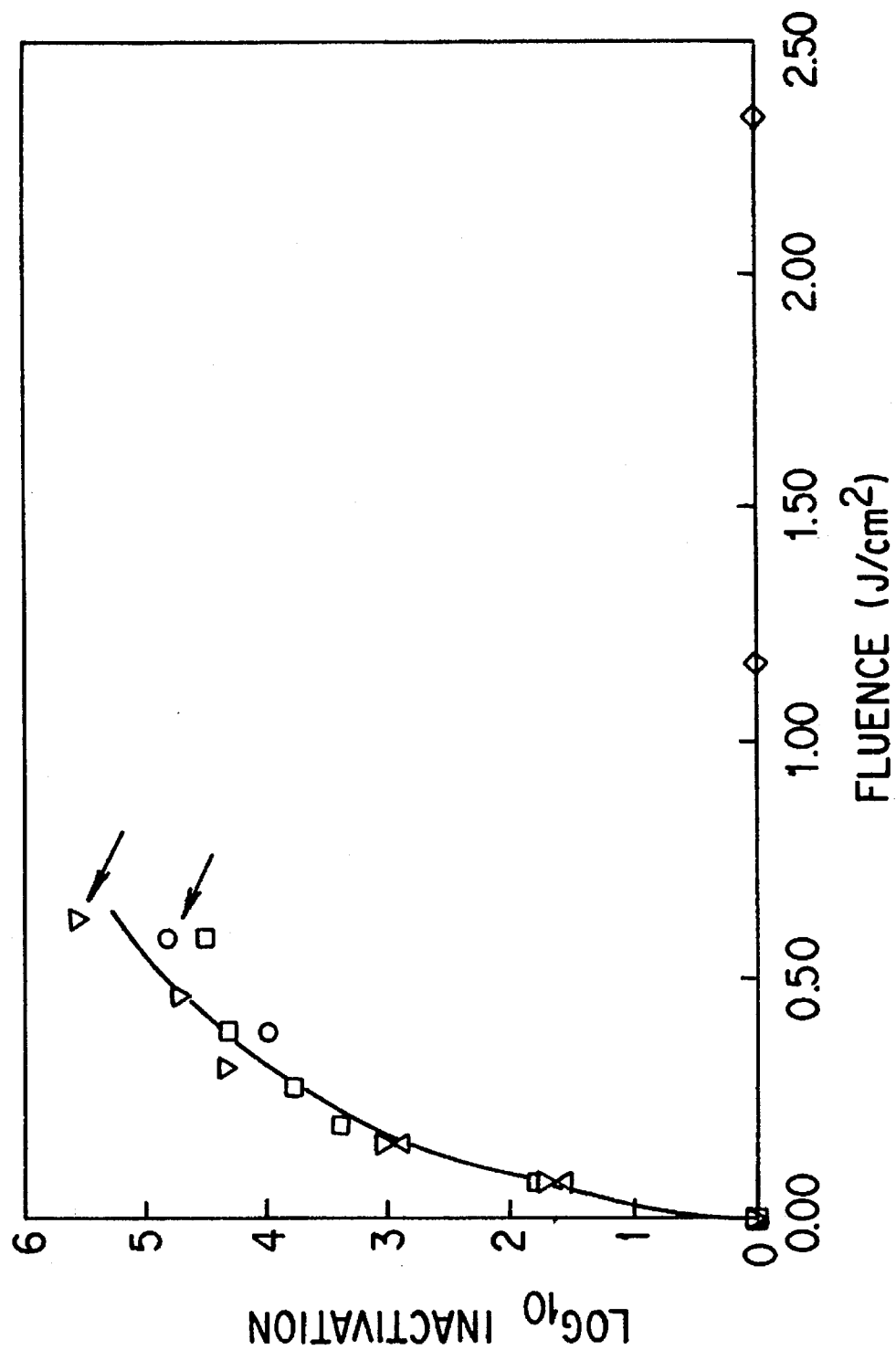
FIG. 5 depicts the linear relationship seen between the inactivating effect of methylene blue (5 μM) on samples of Sindbis virus-infected red blood cells ($log_{10}$), and exposure to an increasing fluence of light ($J/cm^2$). Each open symbol represents an experiment performed on red blood cells derived from a different individual. Arrows depict the limit of sensitivity of the assay.

FIG. 5 shows that more than 5 $\log_{10}$ Sindbis virus was inactivated by 5 µM MB and light. Each type of open symbol in FIG. 5 represents results from an experiment performed on red cells derived from a different individual. Arrows depict the limit of sensitivity of the assay. The Togavirus, Sindbis, is considered to be a surrogate for hepatitis C (HCV) in Applicant's laboratory because a quantitative culture system for HCV has not yet been developed. Although HCV and Sindbis virus are only distantly related, they have nevertheless been previously grouped under the Togavirus family and share a distant sequence and structural relationship (Choo et al., *Science* 244:359–362 (1989); Miller et al., *Proc. Natl. Acad. Sci. USA* 87:2057–2061 (1990); copies attached). The Sindbis virus is extremely sensitive to MB photoinactivation.

EXAMPLE 21

Extracellular encephalomyocarditis (EMC) virus was not inactivated using the methods of this invention. The methods used were the same methods as were used to inactivate the Sindbis virus as described in Example 20. The only difference was that 1% $MgCl_2$ was included in the EMC overlay medium. EMC is a nonenveloped RNA-containing virus (see, *Virology: Directory and Dictionary of Animal, Bacterial and Plant Viruses* (Hull et al., eds.) Stockton Press, 15 East 26th Street, New York, N.Y. 10010, U.S.A. (1989) pp. 70 and 168, attached).

I claim:

1. A method for inactivating extracellular enveloped viruses which are present in a leukocyte-containing transfusible composition, comprising:

(a) leukodepleting said composition by a factor of at least 5 $\log_{10}$;

(b) adding an adequate amount of at least one phenothiazin-5-ium dye to said leukodepleted composition of step (a), to produce therein an effective concentration of said dye(s), wherein said concentration is acceptable for transfusion and wherein said concentration in conjunction with light is effective to inactivate extracellular enveloped viruses contained in said composition; and (c) irradiating said phenothiazin-5-ium dye-containing composition of step (b) for an effective length of time, with light of effective intensity and wavelengths which are absorbed by said dye(s), whereby said irradiation in conjunction with said dye(s) inactivate extracellular enveloped viruses in said composition.

2. A method for inactivating extracellular enveloped viruses which are present in a leukocyte-containing, red blood cell-containing composition, comprising:

(a) leukodepleting said composition;

(b) adding an adequate amount of at least one phenothiazin-5-ium dye to said composition to produce therein an effective concentration of said dye(s), wherein said concentration is acceptable for transfusion and wherein said concentration in conjunction with light is effective to inactivate extracellular enveloped viruses contained in said composition; and (c) irradiating said phenothiazin-5-ium dye-containing composition for an effective length of time, with light of an effective intensity and of wavelengths which are absorbed by said dye(s), whereby said irradiation in conjunction with said dye(s) inactivate extracellular enveloped viruses in said composition, wherein said red blood cells retain their viability.

3. A method for inactivating extracellular enveloped viruses which are present in a leukocyte-containing, platelet-containing composition, comprising:

(a) leukodepleting said composition;

(b) adding an adequate amount of at least one phenothiazin-5-ium dye to said composition to produce therein an effective concentration of said dye(s), wherein said concentration is acceptable for transfusion and wherein said concentration in conjunction with light is effective to inactivate extracellular enveloped viruses contained in said composition; and (c) irradiating said phenothiazin-5-ium dye-containing composition for an effective length of time, with light of an effective intensity and of wavelengths which are absorbed by said dye(s) whereby said irradiation in conjunction with said dye(s) inactivate extracellular enveloped viruses in said composition, wherein said platelets retain their viability.

4. A method for inactivating extracellular enveloped viruses which are present in leukocyte-containing plasma, comprising:

(a) leukodepleting said plasma by a factor of at least 5 $\log_{10}$;

(b) adding an adequate amount of at least one phenothiazin-5-ium dye to said leukodepleted plasma of step (a) to produce therein an effective concentration of said dye(s), wherein said concentration is acceptable for transfusion and wherein said concentration in conjunction with light is effective to inactivate extracellular enveloped viruses contained in said composition; and (c) irradiating said phenothiazin-5-ium dye-containing plasma of step (b) for an effective length of time, with light of an effective intensity and of wavelengths which are absorbed by said dye(s), whereby said irradiation in conjunction with said dye(s) inactivate extracellular enveloped viruses in said plasma.

5. The method of claim 4, wherein said plasma contains ARC-8.

6. The method of claim 4, wherein said plasma is transfusible.

7. The method of claim 4, wherein the plasma concentration is from 2.5% to 100%.

8. The method of claim 4, wherein the plasma concentration is from 50% to 100%.

9. The method of any one of claims 1–4, wherein said phenthiazin-5-ium dye is selected from the group consisting of methylene blue, toluidine blue O, azure A, azure B, azure C and thionine.

10. The method of claim 9, wherein said dye is methylene blue.

11. The method of claim 9, wherein said dye is toluidine blue O.

12. The method of claim 9, wherein said dye is thionine.

13. The method of claim 9, wherein said phenthiazin-5-ium dye is U.S.P. grade.

14. The method of any one of claims 1–4, wherein said effective inactivating concentration of the phenthiazin-5-ium dye(s) is from 0.2 μM to 50 μM.

15. The method of any one of claims 1–4, wherein said effective inactivating concentration of the phenthiazin-5-ium dye(s) is from 1 μM to 25 μM.

16. The method of any one of claims 1–4, wherein said effective inactivating concentration of the phenthiazin-5-ium dye(s) is from 1 μM to 5 μM.

17. The method of any one of claims 1–4, wherein said effective length of irradiation time is from 1 minute to 120 minutes.

18. The method of any one of claims 1–4, wherein said effective length of irradiation time is from 90 minutes to 120 minutes.

19. The method of any one of claims 1–4, wherein said extracellular enveloped viruses are selected from the group consisting of RNA viruses and DNA viruses.

20. The method of claim 19, wherein said enveloped RNA virus is a retrovirus.

21. The method of claim 20, wherein said extracellular retrovirus is human immunodeficiency virus −1.

22. The method of claim 19, wherein said RNA virus is bacteriophage φ6.

23. The method of claim 19, wherein said extracellular enveloped DNA virus is selected from the group consisting of: herpes viruses; hepatitis B virus; pox viruses; and cytomegaloviruses.

24. The method of claim 19, wherein said extracellular enveloped DNA virus is pseudorabies virus.

25. The method of claim 19, wherein said extracellular enveloped RNA virus is selected from the group consisting of: hepatitis A virus; hepatitis C virus; paramyxoviruses; and toga viruses.

26. The method of claim 19, wherein said extracellular enveloped RNA virus is Sindbis virus.

27. The method of any one of claims 1, 3 or 4, wherein said extracellular enveloped virus is vesicular stomatitis virus.

28. The method of any one of claims 1–3, wherein said leukocyte-containing composition contains ARC-8.

29. The method of any one of claims 1–3, wherein said leukocyte-containing composition is whole blood.

30. The method of any one of claims 1–3, wherein said leukocyte-containing composition contains plasma.

31. The method of either one of claims 2 or 3, wherein the resulting leukodepleted composition is a transfusible composition of step (c).

32. A process for treating a leukocyte-containing red blood cell-containing composition in order to inactivate any extracellular lipid enveloped human pathogenic virus contained therein without incurring substantial disruption or inactivation of said cells, comprising:

(a) leukodepleting said composition;

(b) contacting said red blood cell-containing composition having a concentration of red blood cells $\geq 1 \times 10^9$ cells/ml with a viricidally effective amount of at least one phenothiazin-5-ium dye, with light and with ambient oxygen to inactivate said virus if present therein and to effect a virus kill of at least 4 $\log_{10}$.

33. A process according to claim 32, wherein extracellular lipid enveloped virus is inactivated.

* * * * *